United States Patent
Ozaki et al.

(10) Patent No.: US 10,201,809 B2
(45) Date of Patent: Feb. 12, 2019

(54) PHOTOCATALYST SHEET

(71) Applicant: NITTO DENKO CORPORATION, Osaka (JP)

(72) Inventors: Takashi Ozaki, Osaka (JP); Masayuki Minakata, Osaka (JP); Keita Mine, Osaka (JP); Daniel Popovici, Osaka (JP); Toshitaka Nakamura, Osaka (JP); Tao Gu, Oceanside, CA (US); Brett T. Harding, Oceanside, CA (US); Takuya Fukumura, Osaka (JP); Guang Pan, Oceanside, CA (US); Ekambaram Sambandan, Oceanside, CA (US); Rajesh Mukherjee, Oceanside, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 14/903,038

(22) PCT Filed: Jul. 4, 2014

(86) PCT No.: PCT/JP2014/068523
§ 371 (c)(1),
(2) Date: Jan. 5, 2016

(87) PCT Pub. No.: WO2015/002326
PCT Pub. Date: Jan. 8, 2015

(65) Prior Publication Data
US 2016/0158738 A1 Jun. 9, 2016

Related U.S. Application Data

(60) Provisional application No. 61/843,267, filed on Jul. 5, 2013, provisional application No. 61/898,980, filed
(Continued)

(30) Foreign Application Priority Data

Oct. 22, 2013 (JP) .................................. 2013-218875
May 30, 2014 (JP) .................................. 2014-113003

(51) Int. Cl.
*B01J 35/00* (2006.01)
*B01J 35/02* (2006.01)
(Continued)

(52) U.S. Cl.
CPC ............. *B01J 35/004* (2013.01); *A61L 2/088* (2013.01); *B01D 53/8687* (2013.01);
(Continued)

(58) Field of Classification Search
None
See application file for complete search history.

(56) References Cited

U.S. PATENT DOCUMENTS

| 4,917,820 A | 4/1990 | Matsumoto et al. |
| 4,955,208 A | 9/1990 | Kawashima |

(Continued)

FOREIGN PATENT DOCUMENTS

| CN | 1805780 A | 7/2006 |
| EP | 0261422 | 3/1988 |

(Continued)

OTHER PUBLICATIONS

Hess, Hess's Paint Film Defects, 1979.*
(Continued)

*Primary Examiner* — Melvin C. Mayes
*Assistant Examiner* — Stefanie J Cohen
(74) *Attorney, Agent, or Firm* — K&L Gates LLP; Louis C. Cullman; Hal Gibson

(57) ABSTRACT

There is provided a photocatalyst sheet comprising a base material and a photocatalyst layer containing at least a
(Continued)

photocatalyst, wherein the photocatalyst layer is firmly adhered to the base material. In an embodiment, there is provided a photocatalyst sheet comprising a base material; and a photocatalyst layer that contains at least a photocatalyst, and is formed on at least one surface of the base material through an aerosol deposition method. This photocatalyst sheet has an excellent photocatalytic activity and an excellent adhesion.

12 Claims, 13 Drawing Sheets

Related U.S. Application Data on Nov. 1, 2013, provisional application No. 61/899,799, filed on Nov. 4, 2013, provisional application No. 61/899,804, filed on Nov. 4, 2013, provisional application No. 61/944,879, filed on Feb. 26, 2014, provisional application No. 61/946,611, filed on Feb. 28, 2014, provisional application No. 61/955,466, filed on Mar. 19, 2014.

(51) Int. Cl.
  *B01J 35/06* (2006.01)
  *B01J 37/02* (2006.01)
  *B01J 23/30* (2006.01)
  *B01J 23/72* (2006.01)
  *B01J 23/835* (2006.01)
  *A61L 2/08* (2006.01)
  *B01D 53/86* (2006.01)
  *B01D 53/88* (2006.01)
  *B01J 37/34* (2006.01)
  *B01J 37/06* (2006.01)
  *B01J 35/10* (2006.01)

(52) U.S. Cl.
  CPC ............ *B01D 53/885* (2013.01); *B01J 23/30* (2013.01); *B01J 23/72* (2013.01); *B01J 23/835* (2013.01); *B01J 35/02* (2013.01); *B01J 35/06* (2013.01); *B01J 37/02* (2013.01); *B01J 37/0215* (2013.01); *B01J 37/0217* (2013.01); *B01J 37/0228* (2013.01); *B01J 37/341* (2013.01); *B01D 2255/2065* (2013.01); *B01D 2255/2094* (2013.01); *B01D 2255/20707* (2013.01); *B01D 2255/20761* (2013.01); *B01D 2255/20776* (2013.01); *B01D 2255/802* (2013.01); *B01D 2257/708* (2013.01); *B01J 35/1009* (2013.01); *B01J 37/0219* (2013.01); *B01J 37/0232* (2013.01); *B01J 37/0244* (2013.01); *B01J 37/06* (2013.01); *B01J 37/347* (2013.01)

(56) References Cited

U.S. PATENT DOCUMENTS

| | | | |
|---|---|---|---|
| 5,015,282 A | 5/1991 | Takahashi | |
| 5,253,488 A | 10/1993 | Kim et al. | |
| 5,416,060 A | 5/1995 | Yamamoto et al. | |
| 6,770,337 B2 | 8/2004 | Debe et al. | |
| 7,296,422 B2 | 11/2007 | Strohm et al. | |
| 7,641,940 B1 | 1/2010 | Linkous | |
| 7,897,252 B1 | 3/2011 | Linkous | |
| 7,947,318 B2 | 5/2011 | Tracy | |
| 8,029,554 B2 | 10/2011 | Holman et al. | |
| 8,287,611 B2 | 10/2012 | You et al. | |
| 8,293,171 B2 | 10/2012 | Haven | |
| 8,361,539 B2 | 1/2013 | Wu et al. | |
| 8,628,726 B2 | 1/2014 | Pham-Huu et al. | |
| 2002/0170236 A1 | 11/2002 | Larson | |
| 2003/0050196 A1* | 3/2003 | Hirano | A61L 9/00 507/238 |
| 2004/0258581 A1 | 12/2004 | Wei et al. | |
| 2005/0129589 A1 | 6/2005 | Wei et al. | |
| 2006/0076237 A1* | 4/2006 | Pluskal | B01D 57/02 204/450 |
| 2006/0163566 A1* | 7/2006 | Kawaraya | C23C 24/00 257/43 |
| 2009/0052195 A1 | 2/2009 | Saneto et al. | |
| 2009/0233243 A1 | 9/2009 | Kobayashi et al. | |
| 2009/0267270 A1 | 10/2009 | Murakami et al. | |
| 2010/0276638 A1 | 11/2010 | Liu | |
| 2011/0123694 A1 | 5/2011 | Ryska et al. | |
| 2011/0143924 A1* | 6/2011 | Hisata | C09D 5/1618 502/159 |
| 2011/0262312 A1 | 10/2011 | Pham-Huu et al. | |
| 2012/0070334 A1 | 3/2012 | Ehrhorn | |
| 2012/0198862 A1 | 8/2012 | Arrigo | |
| 2013/0011617 A1 | 1/2013 | Tasaki et al. | |
| 2013/0043433 A1 | 2/2013 | Liu et al. | |
| 2013/0168138 A1 | 7/2013 | Yamazaki et al. | |

FOREIGN PATENT DOCUMENTS

| | | | |
|---|---|---|---|
| EP | 0911078 | | 4/1999 |
| EP | 0931581 | | 7/1999 |
| EP | 1251884 | | 7/2006 |
| EP | 2525173 | | 11/2012 |
| EP | 2559744 | | 2/2013 |
| JP | 07-090148 | | 10/1995 |
| JP | 10338854 | | 12/1998 |
| JP | 2000325444 | | 11/2000 |
| JP | 2002-028412 | | 1/2002 |
| JP | 2003-053194 | | 2/2003 |
| JP | 2003093485 | | 2/2003 |
| JP | 2004352957 A | * | 12/2004 |
| JP | 2005-160494 | | 6/2005 |
| JP | 2006-223939 | | 8/2006 |
| JP | 2006-305563 | | 11/2006 |
| JP | 2006307040 | | 11/2006 |
| JP | 2006307040 A | * | 11/2006 |
| JP | 2009-233590 | | 10/2009 |
| JP | 2011-212613 | | 10/2011 |
| KR | 20080108171 A | | 12/2008 |
| WO | 1990002572 | | 3/1990 |
| WO | 1991009823 | | 7/1991 |
| WO | 2007026387 A2 | | 3/2007 |
| WO | 2007147743 | | 12/2007 |
| WO | 2007147744 | | 12/2007 |
| WO | 2012155907 | | 11/2012 |
| WO | WO 2013002151 A1 * | 1/2013 | ............ A01N 59/20 |

OTHER PUBLICATIONS

Kim et al, Effect of Film Thickness on the Photocatalytic Performance of TiO2 Film Fabricated by Room Temperature Powder Spray in Vacuum Process, journal of the korean ceramic society, vol. 45, issue 12 (English) (Year: 2008).*

Kim et al, Effect of Film Thickness on the Photocatalytic Performance of TiO2 Film Fabricated by Room Temperature Powder Spray in Vacuum Process, journal of the korean ceramic society, vol. 45, No. 12, pp. 839-844 (Year: 2008).*

Polisetti et al, photocatalytic activity of combustion synthesized ZrO2 and ZrO2—TiO2 mixed oxides, industrial and engineering chemistry research, 50, pp. 12915-12924 (Year: 2011).*

Mekprasart et al, synthesis and characterization of nitrogen- doped TiO2 and its photocatalytic activity enhancement under visible light, energy procedia 9, pp. 509-514 (Year: 2011).*

Shin et al, activites of CeO2—TiO2 catalyst for SCR of NO with NH3 at low temperature according to operating conditions, Jan. 2013 (Year: 2013).*

Kambur et al, Preparation, characterization and photocatalytic activity of TiO2—ZrO2 binary oxide nanoparticles, applied catalysis b: environment, 115-116, pp. 149-158 (Year: 2012).*

(56) References Cited

OTHER PUBLICATIONS

Shan et al, Novel cerium-tungsten mixed oxide catalyst for the selective catalytic reduction of NOx with NH3, Chem. Commun. 47, pp. 8046-8048 (Year: 2011).*
Bandara et al, Highly stable CuO incorporated TiO2 catalyst for photocatalytic hydrogen production from H2O, the royal society of chemistry and owner societies, photochem. photobiol. sci, 4, pp. 857-861 (Year: 2005).*
International Search Report of PCT/JP2014/068523 dated Jan. 8, 2015.
Chen, Liang, et al. "CeO2—WO3 Mixed Oxides for the Selective Catalytic Reduction of Nox by Nh3 Over a Wide temperature Range". Catal Lett 141:1859-1864 (2011).
Supplementary Partial European Search Report, EP14819588.6, dated Apr. 20, 2017.
Supplementary European Search Report, EP 14819588.6, dated Aug. 3, 2017.
Notification of Reasons for Refusal for Japanese App. No. 2016-523092 (dated Jun. 7, 2018).
Tawainese Office Action dated Sep. 29, 2017 for Taiwanese Application No. 103123268 (Original and English translation of office action enclosed).
Natile et al., WO3/CeO2 Nanocomposite Powders: Synthesis, Characterization, and Reactivity. Chem. Mater., 18(14), pp. 3270-3280 (2006).

* cited by examiner

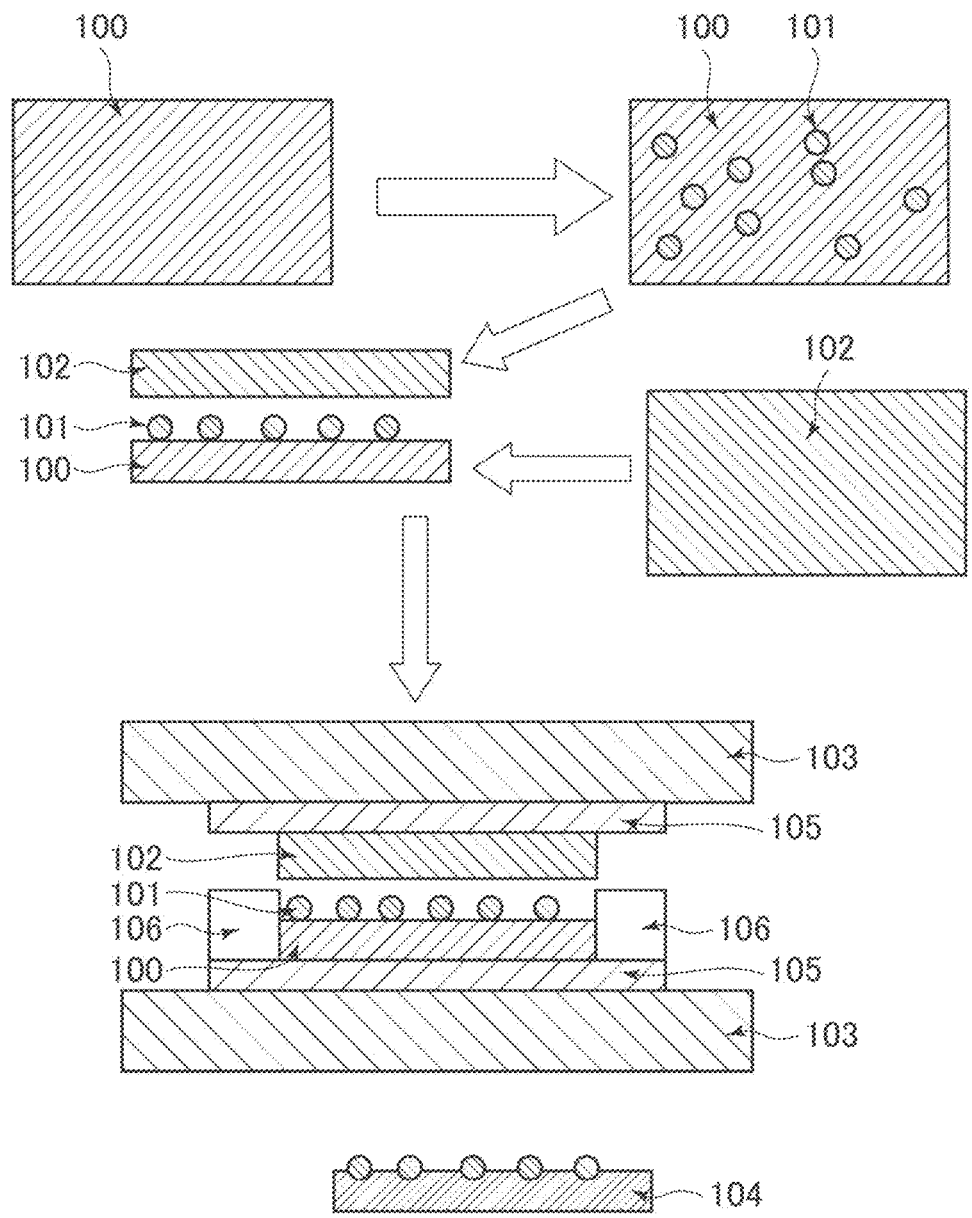

PHOTOCATALYST SHEET

CROSS REFERENCE TO RELATED APPLICATIONS

This application is a national phase of PCT/JP2014/068523 filed on Jul. 4, 2014 which claims priority to U.S. Application No. 61/843,267 filed on Jul. 5, 2013, foreign priority to Japanese Application No. 2013-218875 filed on Oct. 22, 2013, U.S. Application No. 61/898,980 filed on Nov. 1, 2013, U.S. Application No. 61/899,799 filed on Nov. 4, 2013, U.S. Application No. 61/899,804 filed on Nov. 4, 2013, U.S. Application No. 61/946,611 filed on Feb. 28, 2014, U.S. Application No. 61/955,466, and foreign priority Japanese Application No. 2014-113003 filed on May 30, 2014 the entire disclosures of which are incorporated by reference.

TECHNICAL FIELD

The present invention relates to a photocatalyst sheet.

BACKGROUND ART

Photocatalyst sheets have been used for various purposes, including antifouling, sterilizing, and deodorizing applications.

Photocatalyst sheets typically include a plastic film, and a photocatalyst layer made of an oxide semiconductor such as titanium oxide and laminated on a surface of the plastic film (see, for example, Patent Literature 1).

It has been known that the catalyst functions of the photocatalyst sheet such as antifouling property can be improved by increasing the surface area of the photocatalyst layer.

As such a photocatalyst sheet, for example, Patent Literature 2 discloses a photocatalyst sheet configured from a photocatalyst, an adsorbent, and a nonwoven fabric, and in which the nonwoven fabric is covered with the photocatalyst layer.

In Patent Literature 2, the photocatalyst sheet is produced by applying a photocatalyst powder-containing dispersion liquid to the nonwoven fabric, or impregnating the nonwoven fabric with such a dispersion liquid.

CITATION LIST

Patent Literature

PTL1 JP-A-10-338854
PTL2 JP-A-2003-93485

SUMMARY OF INVENTION

A drawback of the photocatalyst sheet of Patent Literature 2, however, is that the photocatalyst layer detaches itself and exfoliates from the nonwoven fabric because of the poor adhesion between the photocatalyst and the nonwoven fabric. As a result, the photocatalyst sheet cannot properly exhibit the desired photocatalyst functions.

In view of the above, the present invention provides a photocatalyst sheet comprising a base material and a photocatalyst layer containing at least a photocatalyst, wherein the photocatalyst layer is firmly adhered to the base material.

Herein, in one embodiment, with an object of providing a photocatalyst sheet having a desirable photocatalytic activity and excellent adhesion of the photocatalyst layer to the base material, there is provided a photocatalyst sheet comprising: a base material; and a photocatalyst layer that contains at least a photocatalyst, and is formed on at least one surface of the base material through an aerosol deposition method.

The photocatalyst sheet according to this embodiment includes a photocatalyst layer formed on a surface of a base material by using an aerosol deposition method. The photocatalyst sheet is thus excellent in photocatalytic activity, and is also excellent in adhesion between the photocatalyst layer and the base material surface. The photocatalyst sheet can thus exhibit excellent antifouling and other photocatalyst functions over extended time periods.

Incidentally, spraying, for example, is known as a method for laminating a photocatalyst layer on a base material such as a nonwoven fabric. However, since the base material is exposed to high temperature in this method, the base material is deteriorated or melted, whereby the adhesion of the photocatalyst layer to the base material becomes lowered.

In addition, Sputtering is another known method. However, there is a problem that the photocatalyst layer laminated by using this method does not have a crystallinity needed to develop the photocatalyst functions, and cannot exhibit its function as the photocatalyst layer. This necessitates a high-temperature treatment for the photocatalyst layer after the sputtering, and thus causes the base material to deteriorate or melt.

Furthermore, bonding photocatalyst particles to the base material with a binder resin may be considered as a way of applying the photocatalyst to the base material. However, embedding the photocatalyst surface with a binder resin lowers the photocatalytic activity. In addition, although the photocatalytic activity can be maintained by reducing the binder amount, this lowers the adhesion to the base material.

In the above-mentioned embodiment wherein the photocatalyst sheet comprises a base material; and a photocatalyst layer that contains at least a photocatalyst and is formed on at least one surface of the base material through an aerosol deposition method, the base material is preferably a porous film.

In the above-mentioned embodiment, the base material is preferably formed of a resin.

In addition, it is preferable that the resin includes at least one selected from the group consisting of a thermosetting resin, a thermoplastic resin, an ultraviolet curable resin, and an electron beam curable resin.

In the above-mentioned embodiment, it is preferable that the photocatalyst shows a visible-light responsiveness.

In the above-mentioned embodiment, the photocatalyst layer may further contain a co-catalyst.

In the above-mentioned embodiment, it is preferable that the photocatalyst contains titanium(IV) oxide or tin(IV) oxide, and the co-catalyst contains copper(I) oxide and/or copper(II) oxide, and that the co-catalyst is supported on the photocatalyst.

In the above-mentioned embodiment, it is preferable that the photocatalyst contains tungsten(VI) oxide, and the co-catalyst contains cerium(IV) oxide.

In addition, there is also provided a method for producing the photocatalyst sheet according to the above-mentioned embodiment, the method comprising forming a photocatalyst layer containing at least a photocatalyst on at least one surface of a base material through an aerosol deposition method.

Furthermore, in an embodiment of a photocatalyst sheet comprising a base material and a photocatalyst layer containing at least a photocatalyst, wherein the photocatalyst layer is firmly adhered to the base material, the photocatalyst may be at least partially embedded in the base material. Examples of methods for forming such a state include the following methods A to C.

Method A: A method for creating a nanoparticle modified surface on a thermoplastic substrate comprising:
  suspending nanoparticles in a solvent;
  applying the suspension to a solvent soluble thermoplastic element;
  allowing the solvent to etch the surface of the substrate a sufficient amount so that the nanoparticles are at least partially embedded in the etched surface of the thermoplastic substrate; and
  removing the solvent from contact with the substrate surface.

Method B: A method for embedding particles into a thermoplastic element comprising:
  coating a donor sheet with a slurry comprising a solvent and particles, wherein the donor sheet material is thermally stable up to a temperature of at least $T_{embed}$, wherein the donor sheet material and particles are substantially insoluble in the slurry solvent;
  baking the donor sheet to evaporate substantially all of the solvent, leaving the particles loosely attached to the donor sheet;
  contacting the substantially dry donor sheet with a thermoplastic element, wherein the surface of the donor sheet comprising the loosely attached particles is in direct contact with the thermoplastic element;
  applying sufficient heat to reach a temperature of $T_{embed}$, wherein $T_{embed}$ is the temperature at which the thermoplastic element is soft enough for embedment of the particles to occur,
  applying sufficient pressure to embed the particles into the thermoplastic element,
  cooling the particle embedded thermoplastic element; and
  separating the particle embedded thermoplastic element from the donor sheet.

Method C: A method for creating a photocatalytic surface on a photocatalytic element comprising:
  providing a photocatalytic element with a surface, the element comprising photocatalytic nanoparticles and a photodegradable polymeric matrix, at least a portion of the photocatalytic nanoparticles adjacent the surface of the polymer matrix surface and covered by the polymeric matrix; and
  irradiating the surface of the polymer matrix a sufficient amount of radiant energy to expose at least some photocatalytic nanoparticles.

In addition, in the above-mentioned embodiment wherein the photocatalyst sheet comprises a base material; and a photocatalyst layer that contains at least a photocatalyst and is formed on at least one surface of the base material through an aerosol deposition method, the photocatalyst may be at least partially embedded in the base material in a certain condition.

BRIEF DESCRIPTION OF DRAWINGS

FIG. 11 illustrates an embodiment of the method of embedding particles into a thermoplastic element.

DESCRIPTION OF EMBODIMENTS

Firstly, some embodiments, wherein the photocatalyst sheet comprises a base material; and a photocatalyst layer that contains at least a photocatalyst and is formed on at least one surface of the base material through an aerosol deposition method, are explained below.

Figure 1:
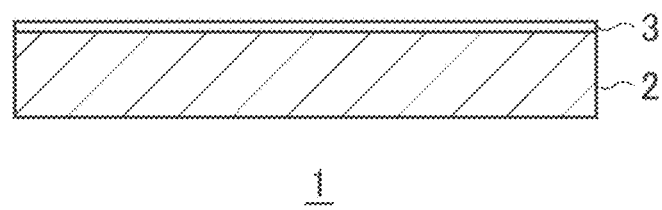
FIG. 1 is a cross sectional view of an embodiment of the photocatalyst sheet of the present invention.

A photocatalyst sheet 1 according to an embodiment shown in FIG. 1 includes a base material 2, and a photocatalyst layer 3 laminated on one surface of the base material 2.

The base material 2 is not particularly limited, and, for example, a non-porous base material, or a porous film may be used. Preferably, a porous film is used as the base material 2 to increase the surface area of the photocatalyst layer to be laminated and thereby further improve the photocatalytic activity thereof.

Examples of the porous film include a nonwoven fabric, a perforated film, a microporous film, and a porous medium. Nonwoven fabric is preferred from the standpoints of improving adhesion of the photocatalyst layer to the base material, and increasing the toughness and surface area of the photocatalyst sheet.

Examples of the material forming the base material 2 include resin, ceramic, and metal. Resin is preferred from the standpoint of the flexibility and lightness of the photocatalyst sheet. Specifically, the base material 2 is preferably made of resin. More preferred as the base material 2 is a porous film made of resin.

Examples of the resin constituting the base material include a thermoplastic resin, a thermosetting resin, an ultraviolet curable resin, and an electron beam curable resin, of which the thermoplastic resin is preferred. Examples of the thermoplastic resin include olefinic resins, for example, such as polyethylene, and polypropylene; polyester resins, for example, such as polyethylene terephthalate (PET); polyamide resins, for example, such as nylon; and cellulose fiber. Preferred are polyester resins.

Examples of the thermosetting resin include epoxy resins, phenolic resins, melamine resins, urea resins, alkyd resins, unsaturated polyester resins, polyurethane, thermosetting polyimides, silicone resins, and diallyl phthalate resins.

Examples of the ultraviolet curable resin include epoxy acrylate resins, and urethane acrylate resins.

Examples of the electron beam curable resin include polyester acrylate resins.

Examples of the metal include copper, iron, and aluminum.

Examples of the ceramic include alumina, silica, titania, zirconia, and mixtures of these.

These may be used either alone or in a combination of two or more.

When the porous film as the base material 2 is a nonwoven fabric, the method used to produce the same is not particularly limited, and it may be produced by using methods, for example, such as a dry method, a wet method, a spunbonding method, a thermal bonding method, a chemical bonding method, a stitch bonding method, a needle punching method, a melt blow method, a spunlacing method, a steam jet method.

The basis weight of the porous film is, for example, 0.1 g/m$^2$ or more, preferably 0.5 g/m$^2$ or more, more preferably 2 g/m$^2$ or more, and, for example, 1,000 g/m$^2$ or less, preferably 500 g/m$^2$ or less, more preferably 100 g/m$^2$ or less.

The thickness of the base material 2 is, for example, 0.1 μm or more, preferably 0.5 μm or more, more preferably 10 μm or more, and, for example, 10,000 μm or less, preferably 1,000 μm or less, more preferably 300 μm or less.

Photocatalyst Layer

The photocatalyst layer 3 is provided on the base material 2. In FIG. 1, the photocatalyst layer 3 is formed over the whole surface on one side of the base material 2. However, the embodiments are not limited thereto, and the photocatalyst layer 3 may be formed only on a part of the surface on one side of the base material 2.

The photocatalyst layer 3 contains at least a photocatalyst. In addition to the photocatalyst, the photocatalyst layer 3 may contain a co-catalyst, as desired. The following describes the photocatalyst contained in the photocatalyst layer 3, and the co-catalyst contained as desired in the photocatalyst layer 3.

Photocatalyst

Photocatalysts are a substance that shows photocatalytic activity upon being irradiated with light of specific wavelengths (excitation light having a higher energy than the band gap between the valence and the conduction band of the photocatalyst). Since photocatalysts shows photocatalytic activity, they can exhibit a wide range of effects, including antimicrobial effect, air refreshment and deodorizing effect, and decomposition of harmful substances such as volatile organic compounds (VOCs).

Examples of the photocatalyst include metal oxides such as anatase-type or rutile-type titanium(IV) oxide ($TiO_2$), tungsten(III) oxide ($W_2O_3$), tungsten(IV) oxide ($WO_2$), tungsten(VI) oxide ($WO_3$), zinc oxide (ZnO), iron(III) oxide ($Fe_2O_3$), strontium titanate ($SrTiO_3$), bismuth(III) oxide ($Bi_2O_3$), bismuth vanadate ($BiVO_4$), tin(II) oxide (SnO), tin(IV) oxide ($SnO_2$), tin(VI) oxide ($SnO_3$), zirconium oxide ($ZrO_2$), cerium(II) oxide (CeO), cerium(IV) oxide ($CeO_2$), barium titanate ($BaTiO_3$), indium(III) oxide ($In_2O_3$), copper (I) oxide ($Cu_2O$), copper(II) oxide (CuO), potassium tantalate ($KTaO_3$), and potassium niobate ($KNbO_3$); metal sulfides such as cadmium sulfide (CdS), zinc sulfide (ZnS), and indium sulfide (InS); metal selenides such as cadmium selenate ($CdSeO_4$), and zinc selenide (ZnSe); and metal nitrides such as gallium nitride (GaN).

The photocatalysts exemplified above may be obtained by using methods, for example, such as solid-phase reaction, combustion synthesis, solvothermal synthesis, pyrolysis, and plasma synthesis. Preferably, the photocatalyst is obtained by using the radio frequency inductively coupled plasma (RF-ICP) technique. RF-ICP has high production efficiency, and can produce a high-purity photocatalyst. For example, the photocatalyst may be obtained under the RF-ICP conditions described in U.S. Pat. No. 8,003,563.

The activity of the photocatalyst can be improved by doping an element of certain species. Such an element may be called a "dopant", and examples of such dopants include alkali metals such as lithium (Li), sodium (Na), potassium (K), and cesium (Cs); alkali earth metals such as magnesium (Mg), calcium (Ca), strontium (Sr), and barium (Ba); noble metals such as gold (Au), platinum (Pt), rhodium (Rh), iridium (Ir), palladium (Pd), and ruthenium (Ru); transition metals such as iron (Fe), titanium (Ti), zinc (Zn), copper (Cu), tungsten (W), manganese (Mn), niobium (Nb), nickel (Ni), zirconium (Zr), and cerium (Ce); other metals such as tin (Sn), and aluminum (Al); metalloids such as boron (B), and arsenic (As); nonmetals such as nitrogen (N), carbon (C), sulfur (S), fluorine (F), and selenium (Se); and compounds containing such metals and nonmetals. In this specification, a photocatalyst doped with a dopant will be referred to as "doped-type photocatalyst".

The term "doping" means adding an arbitrarily chosen element (dopant) to the host compound crystals within a range that essentially does not change the basic crystalline structure of the photocatalyst. Whether the photocatalyst is doped or not can be confirmed by, for example, a peak shift in XPS (X-ray photoelectron spectroscopy). Methods used for forming the doped-type photocatalyst are not particularly limited, and may be, for example, a sol-gel method, a solid-phase reaction method, and an ion implantation method.

When the photocatalyst is a doped-type photocatalyst, the molar ratio of the host compound (compound subjected to doping) and the dopant in the photocatalyst is not particularly limited, and is preferably 99.9:0.1 to 80:20, more preferably 99.9:0.1 to 85:15, further preferably 99.9:0.1 to 87:13.

Preferably, the doped-type photocatalyst is doped with at least one selected from carbon (C), nitrogen (N), sulfur (5), fluorine (F), tin (Sn), zinc (Zn), manganese (Mn), aluminum (Al), selenium (Se), niobium (Nb), nickel (Ni), zirconium (Zr), cerium (Ce), and iron (Fe).

The photocatalyst may be a p-type or an n-type. A p-type photocatalyst may be obtained, for example, by doping a photocatalyst with high valance elements (for example, such as arsenic (As)). An n-type photocatalyst may be obtained, for example, by doping a photocatalyst with low valence elements (for example, such as boron (B)).

It is preferable that the photocatalyst contains a metallic compound (such as an oxide, a nitride oxide, an oxynitride carbide, or a halide), and more preferably contains a titanium compound, a tin compound, or a tungsten compound.

The average oxidation number or formal charge of titanium in the titanium compound is preferably +1 to +6, more preferably +2 to +4, further preferably +1 to +3. The average oxidation number or formal charge of tin in the tin compound is preferably +2 to +8, more preferably +1 to +6, further preferably +1 to +4. The average oxidation number or formal charge of tungsten in the tungsten compound is preferably +1 to +8, more preferably +1 to +6, further preferably +1 to +4.

More specifically, the photocatalyst preferably contains at least one selected from titanium(IV) oxide ($TiO_2$), tin(IV) oxide ($SnO_2$), tungsten(III) oxide ($W_2O_3$), tungsten(IV) oxide ($WO_2$), and tungsten(VI) oxide ($WO_3$). As the titanium(IV) oxide ($TiO_2$), an anatase-type titanium(IV) oxide ($TiO_2$) is preferred.

Incidentally, in the present specification, the phrase that "the photocatalyst contains (comprises) tungsten(VI) oxide ($WO_3$)" includes not only a case where the photocatalyst is a pure tungsten(VI) oxide ($WO_3$) but also a case where the photocatalyst contains a tungsten(VI) oxide ($WO_3$) doped with another element or compound. (The same applies to photocatalysts and co-catalysts other than tungsten oxide.)

Especially, it is preferable that the photocatalyst contains tungsten(VI) oxide ($WO_3$) because it makes it possible to form a photocatalyst layer that shows a sufficient photoactivity with visible light.

The photocatalyst preferably has a refractive index (R1) of 1.0 to 4.0, more preferably 1.0 to 3.0, particularly preferably 1.5 to 2.5 at a wavelength of 589 nm. With the photocatalyst refractive index (R1) falling in the range of 1.0 to 4.0, it becomes easier to reduce the refractive index difference from the co-catalyst, and thus becomes easier to form a translucent photocatalyst layer. Note that the refractive index values of the photocatalyst are measured values obtained with an Abbe refractometer according to the "Solid Sample Measurement Method" specified by JIS K 0062.

The shape of the photocatalyst is not particularly limited, and the photocatalyst is preferably particulate in shape. Incidentally, in the case of using a particulate photocatalyst (photocatalyst particles), the material used for forming the photocatalyst layer may be referred to as a "photocatalyst composition powder".

The average particle size (median diameter) of the photocatalyst particles is not particularly limited, and is, for example, 0.05 μm or more, preferably 0.1 μm or more, and, for example, 50 μm or less, preferably 20 μm or less, more preferably 10 μm or less. The adhesion of the photocatalyst layer 3 to the base material 2 may be improved within these ranges.

The average particle size (median diameter) is measured, for example, by using a particle size distribution measurement device based on a dynamic light scattering method.

The specific surface area (according to BET method) of the photocatalyst particles is, for example, 0.02 $m^2/g$ or more, preferably 0.05 $m^2/g$ or more, more preferably 0.5 $m^2/g$ or more, and, for example, 16.4 $m^2/g$ or less, preferably 8.2 $m^2/g$ or less, more preferably 4.1 $m^2/g$ or less.

The content ratio of the photocatalyst particles in the photocatalyst composition powder is, for example, 5 mass % or more, preferably 10 mass % or more, more preferably 30 mass % or more, and, for example, 100 mass % or less, preferably 95 mass % or less, more preferably 90 mass % or less, most preferably 70 mass % or less.

Co-Catalyst

Co-catalysts are a substance that accelerate the photocatalytic activity of the photocatalyst. The photocatalyst layer according to the embodiments may further contain a co-catalyst, in addition to the photocatalyst, as desired. The co-catalyst may be one that shows or does not show photocatalytic activity by itself. In cooperation with the photocatalyst, the co-catalyst can increase the reaction rate of the photocatalyst by 1.2 fold or more, preferably 1.5 fold or more, further preferably 2.0 fold or more, particularly preferably 3.0 fold or more from that when the photocatalyst is used alone. The reaction rate of the photocatalyst may be based on, for example, the decomposition rate of acetaldehyde, a type of volatile organic compounds (VOCs).

Specifically, the photocatalyst, either alone or with the co-catalyst mixed with or supported by the photocatalyst, is put in a closed space charged with certain quantities of compressed air and acetaldehyde (calibration gas), and irradiated with visible light (wavelength 455 nm, irradiation intensity 200 mW/$cm^2$) for 1 hour. The acetaldehyde concentrations in the closed space before and after the irradiation are then compared to calculate the factor by which the reaction rate of the photocatalyst increased. For example, the acetaldehyde decomposition rate can be said to have increased 3 fold (a 3-fold increase of photocatalytic activity) when the acetaldehyde concentration in a closed space charged with the photocatalyst and the co-catalyst (either mixed with the photocatalyst or supported on the photocatalyst) becomes 20 ppm after the irradiation of the closed space containing 80 ppm of acetaldehyde (i.e., 60 ppm of acetaldehyde has decomposed) as compared to when the acetaldehyde concentration in a closed space charged with the photocatalyst alone becomes 60 ppm after the irradiation of the closed space containing 80 ppm of acetaldehyde (i.e., 20 ppm of acetaldehyde has decomposed).

Examples of the co-catalyst include copper(I) oxide ($Cu_2O$), copper(II) oxide (CuO), yttrium(III) oxide ($Y_2O_3$), molybdenum(VI) oxide ($MoO_3$), manganese(III) oxide ($Mn_2O_3$), gadolinium(III) oxide ($Gd_2O_3$), anatase-type or rutile-type titanium(IV) oxide ($TiO_2$), strontium titanate ($SrTiO_3$), potassium tantalate ($KTaO_3$), silicon carbide (SiC), potassium niobate ($KNbO_3$), silicon oxide ($SiO_2$), tin(IV) oxide ($SnO_2$), aluminum(III) oxide ($Al_2O_3$), zirconium oxide ($ZrO_2$), iron(III) oxide ($Fe_2O_3$), iron(II, III) oxide ($Fe_3O_4$), nickel(II) oxide (NiO), niobium(V) oxide ($Nb_2O_5$), indium oxide ($In_2O_5$), tantalum oxide ($Ta_2O_5$), cerium(II) oxide (CeO), cerium(IV) oxide ($CeO_2$), $A_rX_tO_s$ (where A is a rare earth element, X is an element other than rare earth elements, or a combination of elements other than rare earth elements, r is 1 to 2, t is 0 to 3, and s is 2 to 3), ammonium phosphomolybdate trihydrate (($N_4)_3$[$PMo_{12}O_{40}$]), 12-tungstophosphoric acid ($PW_{12}O_{40}$), tungsten silicide ($H_4$[$SiW_{12}O_{40}$]), phosphomolybdic acid ($12MoO_3H_3PO_4$), and cerium-zirconium composite oxide ($Ce_xZr_yO_2$) (y/x=0.001 to 0.999).

The co-catalyst may be simply mixed with the photocatalyst, or may be supported on the photocatalyst. In this specification, a photocatalyst supporting the co-catalyst is referred to as "supporting-type photocatalyst". The co-catalyst is preferably supported on the photocatalyst. Consequently, a further higher photocatalytic activity can be exerted. As used herein, the term "supporting" refers to the state where a substance different from the photocatalyst is adhering to the photocatalyst surface. Such an adhering state can be observed, for example, by scanning electron microscopy. Methods used for forming the supporting-type photocatalyst are not particularly limited, and may be, for example, an impregnation method, a photoreduction method, or sputtering. The supporting-type photocatalyst may be formed by using the method described in, for example, U.S. Patent Application 2008/0241542. The co-catalyst may be doped with a dopant. A co-catalyst doped with a dopant will be referred to as doped-type co-catalyst. The compounds and elements used to dope the co-catalyst are as exemplified above in conjunction with the photocatalyst.

The co-catalyst preferably contains at least one selected from a cerium compound, a copper compound, a potassium compound, a strontium compound, a tantalum compound, a niobium compound, and a titanium compound. More preferably, the co-catalyst contains a cerium compound, or a copper compound. The average oxidation number or formal charge of the cerium compound is preferably +2 to +4. The average oxidation number or formal charge of the copper compound is preferably +1 to +2.

In one embodiment, the co-catalyst contains cerium oxide, more preferably cerium(IV) oxide ($CeO_2$). This embodiment is suited for use in decomposition of volatile organic compounds (VOCs). When the co-catalyst contains cerium(IV) oxide ($CeO_2$), it is preferable to dope the cerium (IV) oxide, preferably with tin (Sn). In the tin (Sn)-doped cerium(IV) oxide ($CeO_2$:Sn), the tin (Sn) accounts for preferably 1 mol % to 50 mol %, more preferably 1.5 mol % to 10 mol %, further preferably 1.5 mol % to 10 mol %, particularly preferably 1.5 mol % to 4.5 mol % of the total co-catalyst ($CeO_2$:Sn).

In another embodiment, the co-catalyst contains copper oxide, more preferably copper(I) oxide ($Cu_2O$) and/or copper(II) oxide (CuO). This embodiment is suited for antimicrobial applications. When the co-catalyst contains copper(I) oxide ($Cu_2O$) and/or copper(II) oxide (CuO), it is preferable that the copper(I) oxide ($Cu_2O$) and/or copper(II) oxide (CuO) are supported on the photocatalyst.

The shape of the co-catalyst is not particularly limited, but the co-catalyst is preferably particulate in shape for the same reasons described for the photocatalyst. When the co-catalyst is particulate in shape, the average particle size (medium size) of the co-catalyst is not particularly limited, and is, for example, 0.001 μm or more, preferably 0.05 μm or more, more preferably 0.1 μm or more, and, for example, 50 μm or less, preferably 10 μm or less, more preferably 5 μm or less.

The specific surface area (according to BET method) of the co-catalyst particle is, for example, 0.02 $m^2/g$ or more, preferably 0.1 $m^2/g$ or more, more preferably 0.5 $m^2/g$ or more, and, for example, 16.4 $m^2/g$ or less, preferably 8.2 $m^2/g$ or less, more preferably 4.1 $m^2/g$ or less.

In the case where the photocatalyst composition powder contains co-catalyst particles, the content ratio of the co-catalyst particles in the photocatalyst composition powder is, for example, 5 mass % or more, preferably 10 mass % or more, more preferably 30 mass % or more, and, for example, 95 mass % or less, preferably 90 mass % or less, more preferably 70 mass % or less.

The co-catalyst has a refractive index (R2) of preferably 1.0 to 4.0, more preferably 1.0 to 3.0, particularly preferably 1.5 to 2.5 at 589 nm wavelength. With the co-catalyst refractive index (R2) falling in the range of 1.0 to 4.0, it becomes easier to reduce the refractive index difference from the photocatalyst, and form a desirably translucent photocatalyst layer.

Examples of the photocatalyst described above include a UV responsive photocatalyst that shows photocatalytic activity only with ultraviolet rays of less than 380 nm wavelength, and a visible-light responsive photocatalyst that shows photocatalytic activity also with visible light of 380 nm to 780 nm wavelengths. Herein, the photocatalyst contained in the photocatalyst layer may be a UV responsive photocatalyst or a visible-light responsive photocatalyst, and is preferably a visible-light responsive photocatalyst. The visible-light responsive photocatalyst shows some photoactivity with visible light even without the co-catalyst. The visible-light responsive photocatalyst, in cooperation with the co-catalyst, can thus show even higher photoactivity with visible light. When the photocatalyst is a visible-light responsive photocatalyst, the band gap is, for example, 1.5 eV to 3.5 eV, preferably 1.7 eV to 3.3 eV, more preferably 1.77 eV to 3.27 eV. Note that the photocatalyst may show a visible-light responsiveness in certain photocatalyst and co-catalyst combinations even when the photocatalyst is a UV responsive photocatalyst.

Herein, the photocatalyst is preferably one that shows a visible-light responsiveness. A visible-light responsive photocatalyst can show photocatalytic activity also with a visible-light emitting light source such as a fluorescence lamp and an LED Consequently, a photocatalyst sheet using a photocatalyst showing a visible-light responsiveness can be used in a wider range of applications such as indoor building materials and deodorants.

Photocatalysts may be used either alone or as a mixture of two or more. When two or more photocatalysts are used as a mixture, one of the photocatalysts may function as the co-catalyst of the other photocatalyst. Co-catalysts may also be used alone or as a mixture of two or more.

The photocatalyst layer may contain other compounds (for example, such as a binder resin), in addition to the photocatalyst, or in addition to the photocatalyst and the co-catalyst. As is apparent, such additional compounds in the photocatalyst layer may involve a large refractive index difference from the photocatalyst or the co-catalyst, and sufficient translucency may not be ensured for the photocatalyst layer.

It is accordingly preferable that the photocatalyst layer is configured substantially solely from the photocatalyst, or from the photocatalyst and the co-catalyst. Photocatalyst layer being configured substantially solely from the photocatalyst, or from the photocatalyst and the co-catalyst, means that the photocatalyst, or the photocatalyst and the co-catalyst accounts for at least 80 mass %, preferably at least 90 mass % of the total photocatalyst layer.

When the photocatalyst layer contains the photocatalyst and the co-catalyst, the ratio (molar ratio) of the total photocatalyst and the total co-catalyst is preferably 99.5:0.5 to 16.7:83.3, more preferably 99.5:0.5 to 20:80, further preferably 99.5:0.5 to 50:50.

When the photocatalyst content is less than the lower limit of the foregoing ranges, the co-catalyst will be in excess of the photocatalyst amount, and the photocatalyst layer may fail to show sufficient photocatalytic activity. On the other hand, when the photocatalyst content exceeds the upper limit of the foregoing ranges, the co-catalyst will be deficient relative to the photocatalyst amount, and the photocatalyst layer may fail to show sufficient photocatalytic activity.

When the photocatalyst layer contains the photocatalyst and the co-catalyst, the absolute value of the difference between the photocatalyst refractive index (R1) and the co-catalyst refractive index (R2) at 589 nm wavelength (|R1−R2|) is preferably 0 to 035, more preferably 0 to 0.30, further preferably 0 to 0.20, particularly preferably 0 to 0.16. Note that |R1−R2|=0 means that the photocatalyst refractive index (R1) and the co-catalyst refractive index (R2) are the same.

With the refractive index difference of the photocatalyst and the co-catalyst falling in the foregoing ranges, light more easily passes through the photocatalyst layer than being refracted therein (the photocatalyst layer will have increased translucency). This makes it possible to form a photocatalyst layer having superior translucency.

Herein, when the photocatalyst layer contains the photocatalyst and the co-catalyst, the combination of the photocatalyst and the co-catalyst contained in the photocatalyst layer is not particularly limited.

In a preferred embodiment, the photocatalyst contains titanium(IV) oxide ($TiO_2$) or tin(IV) oxide ($SnO_2$), and the co-catalyst contains copper(I) oxide ($Cu_2O$) and/or copper (II) oxide (CuO). In this case, the co-catalyst containing copper(I) oxide ($Cu_2O$) and/or copper(II) oxide (CuO) is preferably supported on the photocatalyst containing titanium(IV) oxide ($TiO_2$) or tin(IV) oxide ($SnO_2$). A photocatalyst layer that is excellent in visible-light responsiveness and photocatalytic activity, and is also particularly excellent in anti-microbial properties can be formed by using titanium (IV) oxide ($TiO_2$) or tin(IV) oxide ($SnO_2$) as the photocatalyst, and copper(I) oxide ($Cu_2O$) and/or copper(II) oxide (CuO) as the co-catalyst. In this specification, a co-catalyst-supporting type photocatalyst supporting a co-catalyst $Cu_xO$ on a photocatalyst $TiO_2$ may be represented by $Cu_xO$—$TiO_2$. Similarly, a co-catalyst-supporting type photocatalyst supporting a co-catalyst $Cu_xO$ on a photocatalyst $SnO_2$ may be represented by $Cu_xO$—$SnO_2$. Here, "$Cu_xO$" is intended to mean a state where two types of copper oxides, CuO (X=1; copper(II) oxide) and $Cu_2O$ (X=2; copper(I) oxide) are present.

In another preferred embodiment, the photocatalyst contains tungsten(VI) oxide ($WO_3$), and the co-catalyst contains cerium(IV) oxide ($CeO_2$). A photocatalyst layer that is excellent in visible-light responsiveness and photocatalytic activity, and is also particularly excellent in the ability to decompose volatile organic compounds (VOCs) can be formed by using tungsten(VI) oxide ($WO_3$) as the photocatalyst, and cerium(IV) oxide ($CeO_2$) as the co-catalyst.

The visible light transmittance of the photocatalyst layer is preferably 70% or more, more preferably 80% or more, particularly preferably 90% or more. The transmittance of the photocatalyst layer for light having a wavelength of 589 nm is preferably 80% or more, more preferably 90% or more.

The visible light transmittance value is a measured value according to JIS R 3106.

A method for producing the photocatalyst sheet 1 is described below.

According to this method, the above-mentioned base material 2 is firstly prepared.

The photocatalyst layer 3 is then formed on one side (surface) of the base material 2 through an aerosol deposition (AD) method.

Figure 2:
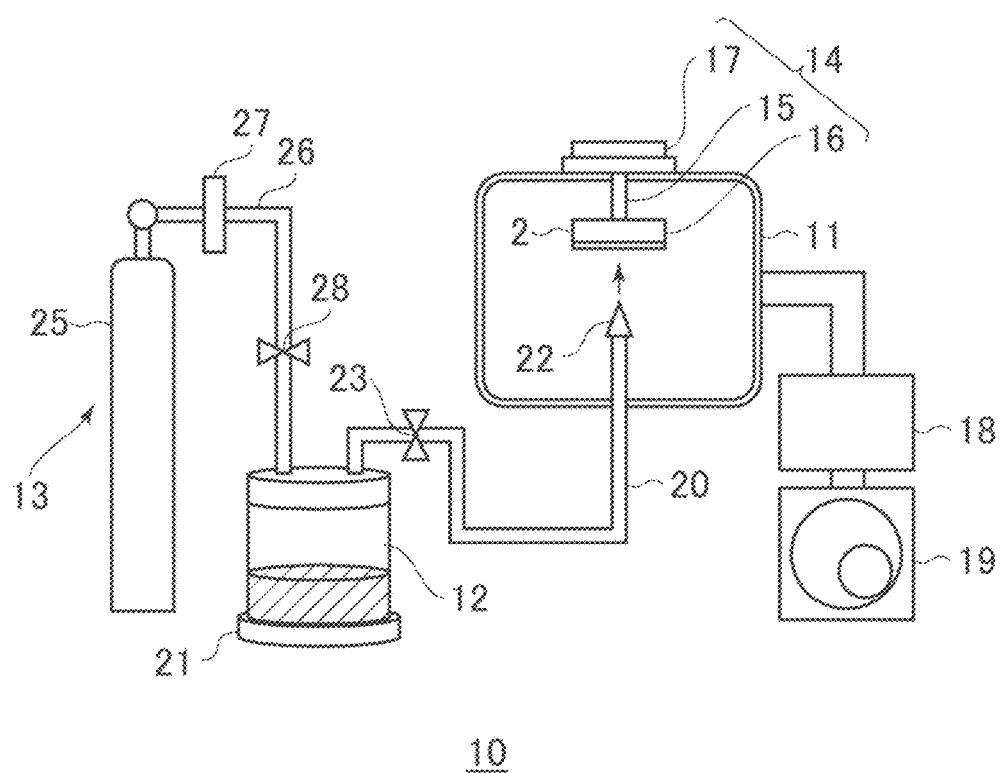
FIG. 2 is a schematic diagram representing the structure of an aerosol deposition apparatus used for a producing method of the photocatalyst sheet shown in FIG. 1.

For the formation of the photocatalyst layer 3 by an aerosol deposition method (AD method; or gas deposition method), for example, an aerosol deposition apparatus 10 shown in FIG. 2 is used.

The aerosol deposition apparatus 10 includes a deposition chamber 11, an aerosol chamber 12, and a carrier gas delivering device 13.

The deposition chamber 11 is a deposition room where the photocatalyst layer 3 is formed on the surface of the base material 2, and it includes a substrate holder 14, a thermometer (not illustrated) for measuring the temperature inside the deposition chamber 11, and a pressure gauge (not illustrated) for measuring the pressure inside the deposition chamber 11.

The substrate holder 14 includes a column 15, a seat 16, and a stage 17.

The column 15 is provided through the ceiling wall of the deposition chamber 11, extending downward (vertically below) to join the seat 16 and the stage 17.

The seat 16 is provided at one end (lower end) of the length of the column 15 to hold and fix the base material 2 inside the deposition chamber 11.

The stage 17 is provided on the top surface of the ceiling wall of the deposition chamber 11, and joined to the other end (upper end) of the length of the column 15 to enable the base material 2 to move in any desired directions (x direction (longitudinal direction); y direction (horizontal direction); z direction (vertical direction); and θ direction (rotation direction)) during the formation of the photocatalyst layer 3.

The stage 17 is joined to the seat 16 via the column 15, and enables moving the seat 16.

In addition, a mechanical booster pump 18 and a rotary pump 19 are joined to the deposition chamber 11.

The mechanical booster pump 18 and the rotary pump 19 are joined in series to the deposition chamber 11 to create a reduced pressure inside the deposition chamber 11, and also to create a reduced pressure inside the aerosol chamber 12 in communication with the deposition chamber 11 via a connecting tube 20 (described later).

The aerosol chamber 12 is a reservoir for storing the material (for example, the photocatalyst composition powder) of the photocatalyst layer 3, and includes a vibrator 21, and a pressure gauge (not illustrated) for measuring the pressure inside the aerosol chamber 12.

The vibrator 21 is a device for vibrating the aerosol chamber 12 and the material of the photocatalyst layer 3 inside the aerosol chamber 12. A known shaker is used for the vibrator 21.

Moreover, the connecting tube 20 is joined to the aerosol chamber 12.

The connecting tube 20 is a pipe for delivering the aerosol material (hereinafter, "aerosol") from the aerosol chamber 12 to the deposition chamber 11, and it is disposed such that one end (upstream end) thereof is joined to the aerosol chamber 12 and the other end penetrates through the bottom wall of the deposition chamber 11 so as to extend towards the seat 16. Moreover, inside the deposition chamber 11, a deposition nozzle 22 is joined to the other end (downstream end) of the connecting tube 20.

The deposition nozzle 22 is a jetting device for jetting the aerosol onto the surface of the base material 2. Inside the deposition chamber 11, and the deposition nozzle 22 is disposed in the deposition chamber 11 with its jet orifices facing the seat 16 disposed vertically above. Specifically, the deposition nozzle 22 is disposed opposite and down below the seat 16 with the jet orifices separated from the seat 16 by a predetermined distance (for example, 1 mm or more, preferably 3 mm or more, and, for example, 100 mm or less, preferably 50 mm or less). The aerosol supplied from the aerosol chamber 12 can thus be jetted onto the surface of the base material 2.

The shape of the jet orifices of the deposition nozzle 22 is not particularly limited, and may be appropriately decided according to such factors as the amount and the range of the jetted aerosol.

Moreover, a connecting tube on-off valve 23 is disposed midway through the flow direction of the connecting tube 20. A known on-off valve, for example, such as a solenoid valve may be used as the connecting tube on-off valve 23.

The carrier gas delivering device 13 includes a carrier gas cylinder 25.

The carrier gas cylinder 25 is a cylinder for storing a carrier gas, for example, such as oxygen gas, helium gas, argon gas, nitrogen gas, and air, and is joined to the aerosol chamber 12 via a gas pipe 26.

The gas pipe 26 is a pipe for delivering the carrier gas from the carrier gas cylinder 25 to the aerosol chamber 12.

The gas pipe 26 is joined to the carrier gas cylinder 25 at the upstream end, and to the aerosol chamber 12 at the downstream end.

Moreover, a gas flowmeter 27 is disposed midway through the flow direction of the gas pipe 26. The gas flowmeter 27 is a device for adjusting and detecting the gas flow rate inside the gas pipe 26. The gas flowmeter 27 is not particularly limited, and a known flowmeter may be used.

Furthermore, a gas pipe on-off valve 28 is disposed midway through the flow direction of the gas pipe 26, on the downstream side of the gas flowmeter 27. A known on-off valve, for example, such as a solenoid valve may be used as the gas pipe on-off valve 28.

For the formation of the photocatalyst layer 3 with the aerosol deposition apparatus 10, the deposition nozzle 22 and the base material 2 are disposed to oppose each other with a distance (disposing step). Specifically, the base material 2 is disposed on the seat 16 in such a manner that the surface on which the photocatalyst layer 3 is to be formed faces the deposition nozzle 22 (lower side).

Separately, the material (photocatalyst composition powder) of the photocatalyst layer 3 is charged into the aerosol chamber 12.

Incidentally, the material of the photocatalyst layer 3 may be dried in advance of charging the aerosol chamber 12.

The drying temperature is, for example, 50 to 150° C. The drying time is, for example, 1 to 24 hours.

Thereafter, according to this method, the mechanical booster pump 18 and the rotary pump 19 are driven with the gas pipe on-off valve 28 closed and the connecting tube on-off valve 23 open to create a reduced pressure inside the deposition chamber 11 and the aerosol chamber 12.

The pressure inside the deposition chamber 11 is, for example, 5 to 80 Pa. The pressure inside the aerosol chamber 12 is, for example, 5 to 80 Pa.

Thereafter, according to this method, the material of the photocatalyst layer 3 inside the aerosol chamber 12 is vibrated with the vibrator 21 and also the gas pipe on-off valve 28 is opened, so that the carrier gas is supplied from the carrier gas cylinder 25 to the aerosol chamber 12. This aerosolizes the material of the photocatalyst layer 3, and the generated aerosol is delivered to the deposition nozzle 22 through the connecting tube 20. The aerosol collides with the inner wall of the deposition nozzle 22, and breaks into particles of even smaller particle size.

The flow rate of the carrier gas adjusted with the gas flowmeter 27 is, for example, 0.1 L/min or more, preferably 0.5 L/min or more, and, for example, 20 L/min or less, preferably 18 L/min or less.

Thereafter, according to this method, the disrupted material particles is jetted from the jet orifice of the deposition nozzle 22 onto the surface of the base material 2 (jetting step).

The pressure inside the aerosol chamber 12 during the aerosol jetting procedure is, for example, 50 Pa or more, preferably 1,000 Pa or more, and, for example, 80,000 Pa or less, preferably 50,000 Pa or less. The pressure inside the deposition chamber 11 is, for example, 10 Pa or more, preferably 30 Pa or more, and, for example, 1,000 Pa or less, preferably 800 Pa or less.

Moreover, the temperature inside the aerosol chamber 12 during the aerosol jetting procedure is, for example, 0 to 50° C.

Moreover, it is preferable to appropriately move the stage 17 during the aerosol jetting procedure so that the aerosol can be evenly jetted onto the surface of the base material 2.

In this case, the moving speed of the stage 17 (the moving speed of the deposition nozzle 22) is, for example, 0.1 mm/s or more, preferably 0.2 mm/s or more, and, for example, 30 mm/s or less, preferably 28 mm/s or less.

The photocatalyst layer 3 can thus be formed on the surface (lower side in the vertical direction) of the base material 2 after these procedures. As a result, a photocatalyst sheet 1 provided with the base material 2 and the photocatalyst layer 3 can be obtained (see FIG. 1).

Incidentally, although the stage 17 is moved during the jetting step in the above, it is also possible to move the deposition nozzle 22 in the jetting step so that a relative speed between the base material 2 and the deposition nozzle 22 becomes 0.1 to 30 mm/s, as may be decided according to the aerosol deposition apparatus 10.

The jetting step may be repeated multiple times as may be decided according to the relative speed, and the thickness of the photocatalyst layer 3. Preferably, the jetting step is repeated 2 to 10 times.

The thickness of the photocatalyst layer is not particularly limited. As is evident, excitation light may fail to reach when the photocatalyst layer is too thick. On the other hand, the photocatalyst layer may fail to show sufficient photocatalytic activity when the photocatalyst layer is too thin.

Considering these, the thickness of the photocatalyst layer 3 is, for example, 0.01 μm or more, preferably 0.05 μm or more, more preferably 0.1 μm or more, and, for example, 50 μm or less, preferably 30 μm or less, more preferably 5 μm or less.

The thickness of the photocatalyst layer 3 is the average length as observed in a side cross sectional SEM image of the photocatalyst sheet 1 taken along the thickness direction.

According to this photocatalyst sheet 1, since the photocatalyst layer 3 is formed on the surface of the base material 2 by using an aerosol deposition method, the photocatalyst particles densely and surely adhere to the surface of the base material 2. Further, damage to the base material 2 is prevented because the photocatalyst layer 3 can be provided without subjecting the base material 2 to a high-temperature treatment. The photocatalyst layer 3 can thus have an excellent photocatalytic activity, and also have an excellent adhesion to the surface of the base material 2. The photocatalyst sheet 1 can thus desirably exhibit the antifouling and other photocatalyst functions over extended time periods. Particularly, when the base material 2 is a porous film, the photocatalytic activity can be further improved owing to the increase in the specific surface area of the photocatalyst layer 3, and adhesion of the photocatalyst layer 3 to the base material 2 (porous film) is also excellent. The photocatalyst sheet 1 using a porous film as the base material 2 can thus more desirably exhibit the antifouling and other photocatalyst functions over extended time periods.

The photocatalyst sheet 1 can preferably be used in various applications requiring antifouling, deodorization, and sterilization properties. For example, the photocatalyst sheet 1 is preferred for use in applications such as building walls, deodorizers, air cleaners, sterilizers, and wrapping containers.

Figure 3:
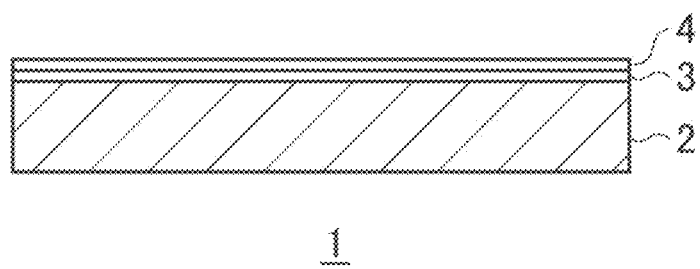
FIG. 3 is a cross sectional view of another embodiment of the photocatalyst sheet of the present invention (a photocatalyst sheet with a co-catalyst layer).

Incidentally, the co-catalyst particles may be contained in the photocatalyst composition powder forming the photocatalyst layer 3, or, for example, a co-catalyst layer 4 formed of co-catalyst particles may be formed on one surface of the photocatalyst layer 3, as shown in FIG. 3.

The co-catalyst layer 4 is formed of co-catalyst particles.

The co-catalyst layer 4 may be obtained, for example, by coating one surface of the photocatalyst layer with a co-catalyst particle dispersion prepared with a dispersion medium such as water, and drying the surface.

The drying temperature is, for example, 40° C. or more, preferably 50° C. or more, and, for example, less than 120° C., preferably 100° C. or less. The drying time is, for example, 0.5 hours or more, preferably 1 hour or more, and, for example, 24 hours or less, preferably 12 hours or less.

The thickness of the co-catalyst layer 4 is, for example, 0.01 μm or more, preferably 0.02 μm or more, more preferably 0.05 μm or more, and, for example, 50 μm or less, preferably 30 μm or less, more preferably 10 μm or less.

The embodiment of FIG. 3 also exerts the similar functions and effects as the embodiment represented in FIG. 1.

Incidentally, in the photocatalyst sheets of some embodiments, layers other than the base material and the photocatalyst layer (in the following, such layers will be referred to also as "other layers") may be further laminated, as required, provided that such addition does not interfere with the object thereof. For example, the base material and the photocatalyst layer may be directly laminated, or via some other layer such as a layer made of silica or a layer made of alumina.

Referring to the photocatalyst sheet 1 according to one embodiment represented in FIG. 1, the photocatalyst layer 3 is formed only on one surface of the base material 2. However, the embodiments are not limited thereto, and, for example, the photocatalyst layer may be formed on the both surfaces of the base material.

The photocatalyst sheets of some embodiments may include more than one base material or more than one photocatalyst layer, provided that it does not interfere with the object thereof. In such a case, it is preferable that at least one of the outermost layers of the photocatalyst sheet is the photocatalyst layer, in order to effectively exerts the photocatalytic activity of the photocatalyst layer upon irradiation with light.

In the followings, the embodiments relating to the above-mentioned "Method A" are described.

Visible light activated photocatalysts can be deployed for self-cleaning, air and water purification and many other interesting applications usually without any post-deployment non-renewable energy costs. This is because the photocatalysts are able to decompose pollutants (like dyes, volatile organic compounds and $NO_x$) using light available in the ambient like solar radiation or indoor and outdoor lighting. With the anticipated rapid adoption of UV-free indoor lighting (like LEDs and OLEDs), it is imperative to find ways to deploy visible-light activated photocatalysts in indoor applications for instance in cleaning room air in domestic, public and commercial spaces especially in confined areas like aircraft, public buildings, etc. Moreover, additional applications for antibacterial surfaces and self-cleaning materials can have wide applicability in the food service, transportation, health care and hospitality sectors.

Thus there is a need for methods to produce various thermoplastic objects with photocatalytic elements embedded in the surfaces thereof, the photocatalytic element being sufficiently bonded to the thermoplastic such that the amount of, and effectiveness of, the photocatalytic element can be maintained for a sufficient period of time despite normal use and cleaning of the objects.

In view of the above, here is provided a method for creating a nanoparticle modified surface on a thermoplastic substrate is described, the method comprising suspending nanoparticles in a solvent; applying the suspension to a solvent soluble thermoplastic element or substrate; allowing the solvent to etch the surface of the substrate a sufficient amount so that the nanoparticles are at least partially embedded in the etched surface of the thermoplastic substrate; and removing the solvent from contact with the substrate surface (Method A). In some embodiments, the method further comprises cooling the thermoplastic. In some embodiments, removing the solvent from contacting the substrate surface can be heating the coated thermoplastic substrate at a temperature below the melting temperature and/or glass transition temperature of the thermoplastic substrate. In some embodiment, removing the solvent comprises heating the coated thermoplastic substrate at a temperature below the glass transition temperature of the substrate. In some embodiments, the solvent comprises cyclopentanone. In some embodiments, the solvent comprises dichloromethane. In some embodiments, the solvent comprises toluene. In some embodiments, the thermoplastic substrate comprises polyethersulfone. In some embodiments, the thermoplastic substrate comprises ethylene-vinyl-acetate.

These and other embodiments are described in greater detail below.

A current consideration can be to provide thermoplastic elements with particles embedded therein, and methods for creating the same. In particular, the method can be useful for embedding photocatalytic particles into a thermoplastic element. The method described herein involves the use of particles embedded in the surface of the thermoplastics which may not require the thermoplastic to be exposed to relatively high temperatures and/or pressure, reducing the costs of manufacture. The method can enable improved particle retention within the thermoplastic substrate which could reduce wear and deterioration of the particle properties. Photocatalytic particle properties include the ability to break down and rapidly deteriorate bacteria, algae, fungus, mold and mildew. In some embodiments, the method described herein, can therefore be used to manufacture a broad range of photocatalytic embedded thermoplastic materials that are useful for sterilizable equipment. The invention described herein provides an inexpensive method to manufacture a particle embedded thermoplastic material, which does not require the exposure of the thermoplastic to heat and/or pressure. This novel method is described below.

In some embodiments, a method for creating a nanoparticle modified surface on a thermoplastic substrate is described, the method comprising suspending nanoparticles in a solvent; applying the suspension to a solvent soluble thermoplastic element; allowing the solvent to etch the surface of the substrate a sufficient amount so that the nanoparticles are at least partially embedded in the etched surface of the thermoplastic substrate; and removing the solvent from contact with the substrate surface. In some embodiments, the method further comprises cooling the thermoplastic. In some embodiments, removing the solvent from contacting the substrate surface can be heating the coated thermoplastic substrate at a temperature ($T_{heating}$) at a temperature low enough to facilitate removal of the solvent yet not substantially effect/degrade/deteriorate the thermoplastic substrate.

The result is a thermoplastic element comprising a surface modified by nanoparticles embedded therein.

In some embodiments, the method can comprise suspending nanoparticles in a solvent. Any suitable solvent can be used. Considerations for selecting a solvent include the solubility of the thermoplastic resin therein, the volatility of the solvent, and the insolubility of the nanoparticles in the solvent.

In some embodiments, the thermoplastic resin is soluble in the selected solvent, e.g., can be a solvent soluble thermoplastic. In some embodiments, at least 0.01 wt %, at least 0.1 wt %, at least 0.25 wt %, at least 0.5 wt %, at least 1 wt %, at least 2 wt % of the thermoplastic material can be totally dissolved in the selected solvent at room temperature.

In some embodiments, the selected solvent can be a relatively volatile solvent. In some embodiments, the solvent has a boiling point (bp) of less than 140° C., of less than 150° C. of less than 160° C., e.g., cyclopentanone about 130° C., methyl ethyl ketone about 80° C., toluene, about 111° C., and dichloromethane, about 39° C.

In some embodiments, the nanoparticle material to be suspended in the selected solvent can be relatively insolvent in the selected solvent. In some embodiments, the selected nanoparticle material can have a solubility of less than 0.001 wt % in the solvent, less than 0.01 wt % in the selected solvent, less than 0.1 Wt % in the selected solvent.

In some embodiments, the solvent is water. In some embodiments, the solvent is an organic solvent. In some embodiments, the solvent is acidic. In some embodiments, the solvent is alkaline. In some embodiments, the solvent has a neutral pH. In some embodiments, the organic solvent is selected from the group consisting of $C_1$-$C_4$ alcohol, $C_2$-$C_5$ ketone, $C_2$-$C_5$ ester, ether, amide, aromatic hydrocarbon, heterocycle, and any combination thereof. In some embodiments, the solvent is selected from the group consisting of isopropanol, methanol, ethanol, cyclopentanone, n-butanol, methyl ethyl ketone, acetone, toluene, xylene, dichloromethane, hexane, propylene glycol methyl ether acetate, N-methylpyrrolidone, N,N-dimethylformamide, N,N-dimethylacetamide, pyridine, and any combination thereof. The particles may be more easily dispersed in one solvent versus another. A good dispersion of particles may be one in which the particles are not agglomerated and in which the particles do not settle down to the bottom of the slurry within several hours or days. It is a consideration in choosing a solvent in which the particles may be well dispersed because this can aid in forming a uniform coating of the particle in the thermoplastic material. In some embodiments the solvent can be selected to provide a stable dispersion of the particles in the solvent.

The particles may also breakdown, oxidize, or react in some way with certain solvents. Therefore an appropriate solvent must be chosen that does not compromise the integrity of the particles. In some embodiments, the solvent is chosen based on the desired chemical compatibility with the particles. In some embodiments, the solvent does not react in any way with the particles. In some embodiments, the solvent is chosen based on the desired chemical compatibility with the thermoplastic element. In some embodiments, the solvent reacts with the thermoplastic element. In some embodiments, the solvent etches the thermoplastic element. The term etching refers to an effect of a solvent on a surface. The solvent affects the surface by partially unraveling the polymer chains, effectively partially dissolving a layer of the thermoplastic.

In some embodiments, particles are selected to embed in the thermoplastic element. In some embodiments, the particles comprise a metal, or metal oxide material. In some embodiments, the particles can be a catalyst or photocatalyst. In some embodiments, the particles can be a metal oxide comprising a photocatalytic compound. A suitable photocatalytic compound can be: doped or undoped $TiO_x$, doped or undoped $WO_x$, doped or undoped, $SnO_x$, doped or undoped $Cu_xO$, doped or undoped $CeO_x$, doped or undoped ZnO, or any combination thereof. In some embodiments, the doped $TiO_x$ compound can be $TiSn(CNO)_2$ as described in U.S. patent application Ser. No. 13/741,191, filed Jan. 14, 2013 (United States Publication No. 2013/0192976, published Aug. 1, 2013) which is incorporated by reference in its entirety. In some embodiments, the photocatalytic compound can be a $Cu_xO$ loaded photocatalytic composite as described in U.S. patent application Ser. No. 13/840,859, filed Mar. 15, 2013; and/or U.S. Provisional Application 61/835,399, filed Jun. 14, 2013, which are incorporated by reference in their entirety. In some embodiments the photocatalytic compound comprises loaded $TiO_x$, loaded $WO_x$, loaded $SnO_x$, loaded $Cu_xO$, loaded $CeO_x$, loaded ZnO, or any combination thereof. In some embodiments, the selected particles can be substantially insoluble in the selected solvent.

In addition, the above-mentioned photocatalyst and co-catalyst can also be used as the particles in some embodiments.

In some embodiments, the selected nanoparticles can be added to the solvent to create a slurry between about 0.1 wt % and 10 wt %. In some embodiments, the slurry can be about 0.1 wt % nanoparticles, about 0.25 wt % nanoparticles, about 0.5 wt % nanoparticles, about 0.75 wt % nanoparticles, about 1 wt % nanoparticles, about 2 wt % nanoparticles, about 3 wt % nanoparticles, about 4 wt % nanoparticles, about 5 wt % nanoparticles, about 6 wt % nanoparticles, about 7 wt % nanoparticles, about 8 wt % nanoparticles, about 9 wt % nanoparticles, about 10 wt % nanoparticles, In some embodiments, the slurry can include nanoparticles in any proportion within the aforementioned range, up to about 10 wt %. In some embodiments, the slurry can be mixed by ultrasonic means. For example, in some embodiments the slurry of nanoparticles in the solvent is mixed by placing in a sonicator such as Aquasonic Model 75HT by VWR Scientific Products for 1 hour.

Figure 4:
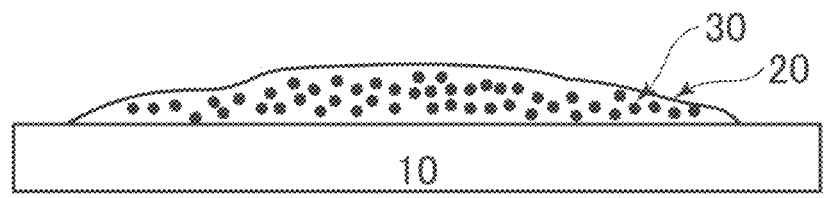
FIG. 4 is a schematic of an element embodiment.

In some embodiments, the method can comprise applying the suspension 20, comprising photocatalytic material 30 to a solvent soluble thermoplastic element 10, as in FIG. 4. Various thermoplastic materials may be used. In some embodiments, the thermoplastic element is selected from the group consisting of acrylic, nylon, polyethylene, polypropylene, polystyrene, polyvinyl chloride, polycarbonate, polyethersulfone (PES), polysulfone, polyether, polyester, polylactic acid, acrylonitrile butadiene styrene (ABS), polyvinyl alcohol, polyvinyl butyral, ethylene vinyl acetate (EVA), ethylene tetrafluoroethylene (ETFE), polytetrafluoroethylene (PTFE), and combinations thereof. In some embodiments, the thermoplastic element comprises PTFE commercially available as Teflon, from Du Pont. In some embodiments, the thermoplastic element comprises PES commercially available as Udel from Union Carbide. In some embodiments, the thermoplastic comprises ETFE commercially available as Tefzel. In some embodiments, the thermoplastic element comprises polycarbonate, PES, ETFE, EVA, and any combination thereof.

In some embodiments, the thermoplastic element can be heated and molded into a desired form or shape before being modified by the method herein disclosed.

Figure 5:
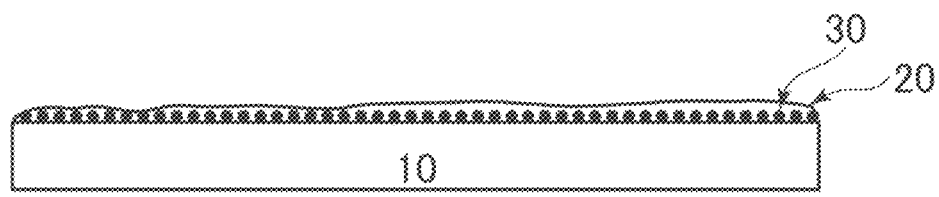
FIG. 5 is a schematic of the element embodiment.

After being applied to the thermoplastic substrate 10, the slurry 30 comprising the photocatalytic material 20, can be coated on the substrate 10, as depicted in FIG. 5. A variety of coating methods may be used to coat the slurry onto the thermoplastic element. In some embodiments, the method of coating the slurry onto the thermoplastic element may be appropriately selected from known methods used to coat liquid substances onto a solid substrate. Specific examples thereof include dip coating, spin coating, drop casting, roll coating, kiss roll coating, gravure coating, reverse coating, roll brush coating, spray coating, dip roll coating, bar coating, knife coating, and air knife coating. In some embodiments, the slurry is coated onto the thermoplastic element by any one of the following methods: dip coating, spin coating, drop casting, roll coating, kiss roll coating, gravure coating, reverse coating, roll brush coating, spray coating, dip roll coating, bar coating, knife coating, and air knife coating. In some embodiments, the thickness of the coating is between 10 nm and 1 mm. In some embodiments, the thickness of the coating is between 100 nm and 500 microns. In some embodiments, the thickness of the coating is between 1 microns and 300 microns. In some embodiments, the thickness of the coating is between 10 microns and 100 microns.

The uniformity and density of the particles embedded into the thermoplastic element may be controlled by the slurry composition and the coating process. A higher concentration of the particles in the slurry will allow a higher density of particles to be embedded into the thermoplastic element. Similarly, the dispersion properties of the slurry may determine the uniformity of the embedded particles on the thermoplastic element. Slurries with well dispersed particles, i.e. no agglomeration, may produce a more uniform surface of embedded particles on the thermoplastic element compared to slurries that are not well dispersed. In some embodiments, the concentration of particles in the slurry is optimized to produce the desired uniformity and density of particles embedded into the thermoplastic element. In some embodiments, the dispersion of the particles in the slurry is optimized to produce the desired uniformity and density of particles embedded into the thermoplastic element. Additionally, the coating process used to coat the slurry onto the thermoplastic element, and the conditions used in the coating process may also affect the uniformity and density of the embedded particles in the thermoplastic element. In some embodiments, the coating process is optimized to produce the desired uniformity and density of particles embedded into the thermoplastic element.

Etching/Mixing

Figure 6:
FIG. 6 is a schematic of the element embodiment.

In some embodiments, the suspension 20 comprises the photocatalytic material 30 and solvent. In some embodiments the solvent etches the surface of the substrate 10 a sufficient amount so that the nanoparticles 30 are at least partially embedded in the etched surface of the thermoplastic substrate 10, as shown in FIG. 6.

In some embodiments, the slurry etches the plastic. The etching process can result in a layer of the thermoplastic element softening and substantially dissolving as the solvent unravels the polymer chains of the thermoplastic. As the thermoplastic is etched, the slurry of solvent and particles mixes with the dissolved thermoplastic polymer layer, distributing the particles throughout the mixture. In some embodiments, the solvent can distribute particles to different depths within the thermoplastic element. The depth to which particles can become embedded in the thermoplastic element depends on a variety of parameters, including but not limited to the reactivity of the thermoplastic to the solvent component of the slurry, the relative solubility of the thermoplastic polymer in the solvent component of the slurry, the length of time the thermoplastic surface is exposed to the slurry, or the relative concentration of the particles in the slurry. A more reactive combination, a longer exposure time of the thermoplastic polymer surface to the slurry solvent, or a more aggressive slurry solvent can result in particles becoming embedded deeper within the surface of the thermoplastic element. For example, if the solvent is cyclopetanone and the thermoplastic element is polyethersulfone (PES) and/or ethylene-vinyl acetate (EVA), then the slurry solvent can be exposed to the thermoplastic surface for less than 3 minutes, less than 5 minutes, less than 7 minutes and/or less than 10 minutes. For example, if the solvent is dichloromethane and the thermoplastic element is polyethersulfone, ethylene-vinyl acetate and/or polycarbonate (PC), then the slurry solvent can be exposed to the thermoplastic surface for less than 3 minutes, less than 5 minutes, less than 7 minutes and/or less than 10 minutes. For example, if the solvent is toluene and the thermoplastic element is polyethersulfone, ethylene-vinyl acetate and/or polycarbonate (PC), then the slurry solvent can be exposed to the thermoplastic surface for less than 3 minutes, less than 5 minutes, less than 7 minutes and/or less than 10 minutes. For example, if the solvent is methyl ethyl ketone and the thermoplastic element is polyethersulfone, ethylene-vinyl acetate and/or polycarbonate (PC), then the slurry solvent can be exposed to the thermoplastic surface for less than 3 minutes, less than 5 minutes, less than 7 minutes and/or less than 10 minutes.

In some embodiments, less than 25%, less than 10%, less than 5% of the thickness of the contacted substrate may be softened to accept nanoparticles therein. An indication that the contacted surface has softened can be indicated by the presence or depth of the nanoparticle material in the hardened thermoplastic. In some embodiments, the nanoparticles are present in less than 25%, less than 10%, less than 5% of the contacted substrate depth or thickness. For example, if the thermoplastic element has a thickness of 1 micron, electron microscope examination of the thermoplastic material exhibits nanoparticles to a depth of less than 25% of the total thickness.

Figure 7:
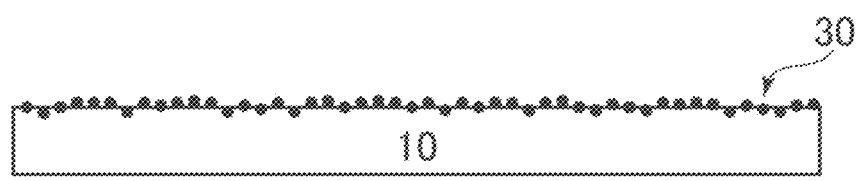
FIG. 7 is a schematic of the element embodiment.
Figure 8:
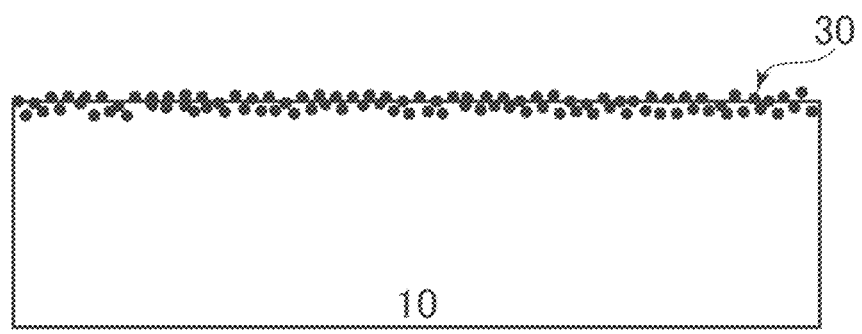
FIG. 8 is a schematic of the element embodiment.

In some embodiments, the embedded particles 30 can be substantially on the surface of the thermoplastic element, with particles having one half or less of the particle exposed, and other particles being completely embedded within the thermoplastic element, as depicted in FIG. 7. In some embodiments, the particles 30 can be embedded to a depth between about 1 nm to about 1 mm below the surface of the thermoplastic element, as depicted in FIG. 8. In some embodiments, the particles can be present to a maximum depth of about 1 nm about 2 nm, about 3 nm, about 4 nm, about 5 nm, about 10 nm, about 20 nm, about 30 nm, about 40 nm, about 50 nm about 100 nm, about 200 nm, about 300 nm, about 400 nm, about 500 nm, about 1 micron, about 2 microns, about 3 microns, about 4 microns, about 5 microns, about 10 micron, about 20 microns, about 30 microns, about 40 microns, about 50 microns, about 100 micron, about 200 microns, about 300 microns, about 400 microns, about 500 microns below the surface of the thermoplastic element. In some embodiments, the particles can be embedded within the thermoplastic element to a depth of any combination of the aforementioned measurements, up to about 1 mm. In some embodiments, the particles are embedded with substantially uniform distribution to the aforementioned depths. In some embodiments, the particles are embedded a maximum of the aforementioned depths. The depth of embedded particles can refer to the distance from the surface of the hardened thermoplastic element to the point where embedded particles are distributed with substantially uniform spacing between particles. Particles may be embedded more deeply within the thermoplastic element, but they become increasingly sparse beyond that depth. The depth of embedded particles can refer to the maximum distance from the surface of the hardened thermoplastic element to the point where embedded particles are present in the thermoplastic element.

Drying/Removal of Solvent

In some embodiments, the method comprises removing the solvent from contacting the thermoplastic surface. After the slurry has etched the thermoplastic element, and the partially dissolved thermoplastic and slurry have mixed, distributing the particles throughout the mixture, the solvent could removed from the thermoplastic element by any appropriate means. Standard methods known in the art can be used to remove the solvent. In some embodiments, the heating of the thermoplastic element is at a sufficient temperature ($T_{heating}$) and/or time to substantially remove substantially all of the solvent without further softening or deforming the thermoplastic element. The heating method, temperature, and time may be chosen appropriately based on the solvent and the particles. In some embodiments, the solvent may evaporate at room temperature after a certain period of time, and therefore the heating or baking temperature may be equal to room temperature. For example, highly volatile solvents such as ethanol or acetone, may not need to be baked at a temperature higher than room temperature as long as a suitable period of time is permitted to substantially evaporate all of said solvent. In some embodiments, the baking temperature may be 100 degrees Celsius, if for instance, the solvent is water. In some embodiments, the baking temperature is adjusted as needed based on the solvent used. Another consideration is that increasing the heating time increases the time the solvent is exposed to the thermoplastic element. The heating time may be sufficient to substantially remove all of the solvent used while maintaining the desired amount of thermoplastic material and/or depth thereof to be effected.

Once the slurry is formed, said slurry can then be coated onto the surface of the substrate, wherein the substrate can be thermally stable up to a temperature of at least $T_{heating}$, e.g., the substrate has a melting temperature and/or a glass transition temperature greater than the $T_{heating}$. In some embodiments of the method, $T_{heating}$ can be at least equal or can be less than the glass transition temperature (Tg) of the thermoplastic element. In some embodiments, $T_{heating}$ can be at least equal to or less than the melting temperature (Tm) of the thermoplastic element. In some embodiments, $T_{heating}$ can be at or near the Tm of the thermoplastic. In some embodiments, $T_{heating}$ can be at least 100 degrees Celsius less than the Tm of the thermoplastic element. In some embodiments, $T_{heating}$ can be at least 80 degrees Celsius less than the Tm of the thermoplastic element. In some embodiments, $T_{heating}$ can be at least 60 degrees Celsius less than the Tm of the thermoplastic element. In some embodiments, $T_{heating}$ can be at least 40 degrees Celsius less than the Tm of the thermoplastic element. In some embodiments, $T_{heating}$ can be at least within 30 degrees Celsius less than the Tm of the thermoplastic element. In some embodiments, $T_{heating}$ can be at least 20 degrees Celsius less than the Tm of the thermoplastic element. In some embodiments, $T_{heating}$ can be at least 10 degrees Celsius less than the Tm of the thermoplastic element. In some embodiments, $T_{heating}$ can be at least 5 degrees Celsius less than the Tm of the thermoplastic element. In some embodiments, the $T_{heating}$ is less than the aforementioned temperature differences relative the Tg. In some embodiments, $T_{heating}$ is between about 50 and about 300 degrees Celsius. In some embodiments, the $T_{heating}$ for a cyclopentanone containing suspension disposed on a polyethersulfone substrate, the heating temperature was about 110° C. and/or about 120° C.

In some embodiments, the heating time can be adjusted as needed to evaporate substantially all of said solvent. Adjusting the pressure of the environment that the thermoplastic element is in can also be used to evaporate the solvent. For example, placing the thermoplastic element in a vacuum chamber at room temperature for a set period of time may be sufficient to evaporate substantially all of the solvent. In some embodiments, the pressure of the environment surrounding the thermoplastic element may be adjusted to evaporate the solvent. In some embodiments, the thermoplastic element can be placed in an oven to evaporate the solvent. In some embodiments, the thermoplastic element may be placed on a hot plate to evaporate the solvent. In some embodiments, the thermoplastic element may be placed in a vacuum oven to evaporate the solvent. In some embodiments, the thermoplastic element may be left at room temperature and pressure for a sufficient period of time to evaporate substantially all of the solvent. In some embodiments, the resultant thermoplastic element may be cooled at a lower temperature to harden the thermoplastic. Coating hardness can be evaluated by following the procedures described in ASTM-3363. Another consideration is that increasing the heating time increases the time the solvent is exposed to the thermoplastic element. The heating time may be sufficient to substantially remove all of the solvent used while maintaining the desired effected amount of thermoplastic material and/or depth thereof.

Resulting Element w/Embedded Particles

In some embodiments, the resulting thermoplastic element has particles embedded within the element such that the presence of particles on the surface will not be affected by abrasion, scratching, or scuffing because the portion of the element removed by the abrasion, scratching, or scuffing merely exposes a fresh layer of the thermoplastic element with particles embedded therein.

In some embodiments, the photocatalytic coating is characterized by an adhesion of about at least 35%, at least 45%, at least 55%, at least 65%, at least 75%, at least 80%, at least 90%, at least 95%, at least 97%, at least 99% adhesion. In some embodiments, a removable percentage of the nanoparticles from the surface of the surface modified thermoplastic material can be a removed percentage of greater than 65% (0B); a removed percentage of 35-65% (1B); a removed percentage of 15-35% (2B); a removed percentage of 5-15% (3B); a removed percentage of less than 5% (4B); and/or a removed percentage of 0% (5B). The term adhesion refers to the percentage of the coating remaining on the substrate after a standard tape removal test method for measuring adhesion. One method of ascertaining the adhesion is by the procedures described in ASTM-D3359.

In some embodiments, a photocatalytic element is described made by the aforedescribed methods. In some embodiments, a photocatalytic element is described, the element comprising photocatalytic nanoparticles and a thermoplastic substrate, the photocatalytic nanoparticles being disposed within the aforementioned distances of the substrate surface.

Next, the embodiments relating to the above-mentioned "Method B" are described below.

A thermoplastic is a polymer that becomes pliable or moldable above a specific temperature, and returns to a solid state upon cooling. The benefit of thermoplastics is that they can be heated and cooled repeatedly without causing damage to the material. In addition, the thermoplastics can be used in a wide range of applications, from bottles, chairs, lights, automobile interiors, police shields, and telephones.

Recently, the use of photocatalytic coated thermoplastic surfaces has become of interest due to the potential for use as sterilizable equipment. Photocatalysts may provide antimicrobial, antibacterial, antifouling, and deodorizing properties, and surfaces that are treated with photocatalysts can be self-cleaning/stain resistant. Many of the various useful objects that can be formed from thermoplastics are improved by the properties of photocatalysts, and so forming thermoplastic objects having a photocatalytic element disposed on the surface is desirable.

Methods for creating photocatalytic coated thermoplastic materials in sterilizable equipment are in need of improvement. Methods of coating photocatalysts onto thermoplastics can include the sol-gel method, and using a binder which contains photocatalysts. Both of these methods are ineffective for long term use as sterilizable equipment because the bond between the photocatalyst and the thermoplastic surface is not strong enough to hold the photocatalyst in place during normal use of the equipment. Other methods require expensive equipment and can be difficult to scale up the process for high volume manufacturing.

One challenge in the art is that coated or embedded particles are not well-bonded to the surface to which they are disposed; and, as the object is used, the photocatalytic elements fall off. As a result, a thermoplastic object with photocatalytic elements can tend to lose the photocatalytic effectiveness as the amount of photocatalytic elements diminishes.

Thus there is a need for scalable methods to produce various thermoplastic objects with photocatalytic elements embedded in the surfaces thereof, the photocatalytic element being sufficiently bonded to the thermoplastic such that the amount of, and effectiveness of, the photocatalytic element can be maintained for a sufficient period of time despite normal use and cleaning of the objects.

In view of the above, disclosed herein is a method that can be used to embed particles into a thermoplastic element. In particular, the method is useful for embedding metal oxide particles into a thermoplastic element. In some embodiments, the method is useful for embedding photocatalytic particles into a thermoplastic element. Prior art methods for applying photocatalytic particles to thermoplastic surfaces have required expensive equipment, or have required the use of a solvent exposure to the thermoplastic material. The inventors have discovered a method for embedding photocatalytic particles into thermoplastic surfaces wherein a donor sheet is used that is both chemically unreactive to the solvent of choice and is thermally stable up to the melting temperature of the thermoplastic element. Using this method, the particles can then be transferred from the donor sheet after the solvent has been evaporated. With this novel method, the ability to embed photocatalytic particles into thermoplastics becomes more diverse because the method is not limited by the compatibility of the solvent to both the photocatalytic particles and the thermoplastic surface. The method described herein, can therefore be used to manufacture a broad range of photocatalytic embedded thermoplastic materials.

In some embodiments, a method of embedding particles into a thermoplastic element comprises the steps of coating a donor sheet with a slurry comprising a solvent and particles, wherein the donor sheet material is thermally stable up to a temperature of at least $T_{embed}$, wherein the donor sheet material and particles are substantially insoluble in the slurry solvent, then baking the donor sheet to evaporate substantially all of the solvent, leaving the particles loosely attached to the donor sheet, then contacting the substantially dry donor sheet with a thermoplastic element, wherein the surface of the donor sheet comprising the loosely attached particles is in direct contact with the thermoplastic element, then applying sufficient heat to reach a temperature of $T_{embed}$, wherein $T_{embed}$ is the temperature at which the thermoplastic element is soft enough for embedment of the particles to occur, then applying sufficient pressure to embed the particles into the thermoplastic element, then cooling the particle embedded thermoplastic element, and separating the particle embedded thermoplastic element from the donor sheet (Method B).

In some embodiments of the method, $T_{embed}$ equals or exceeds the Tg of the thermoplastic element but is equal to or less than the Tm of the thermoplastic element. In some embodiments, $T_{embed}$ is at or near the Tm of the thermoplastic. In some embodiments, $T_{embed}$ is within 100 degrees Celsius of the Tm of the thermoplastic element. In some embodiments, $T_{embed}$ is within 80 degrees Celsius of the Tm of the thermoplastic element. In some embodiments, $T_{embed}$ is within 60 degrees Celsius of the Tm of the thermoplastic element. In some embodiments, $T_{embed}$ is within 40 degrees Celsius of the Tm of the thermoplastic element. In some embodiments, $T_{embed}$ is within 30 degrees Celsius of the Tm of the thermoplastic element. In some embodiments, $T_{embed}$ is within 20 degrees Celsius of the Tm of the thermoplastic element. In some embodiments, $T_{embed}$ is within 10 degrees Celsius of the Tm of the thermoplastic element. In some embodiments, $T_{embed}$ is within 5 degrees Celsius of the Tm of the thermoplastic element. In some embodiments, $T_{embed}$ is between about 50 and about 300 degrees Celsius.

In some embodiments of the method, a heated pressing means is used to simultaneously heat the thermoplastic element up to a temperature of $T_{embed}$ and apply sufficient pressure to embed the particles into the thermoplastic element. In some embodiments, the temperature $T_{embed}$ of the heated pressing means, the pressure applied by the heated pressing means, and the length of time the thermoplastic element and donor sheet are heated and pressed together by the heated pressing means, are variables that must be optimized based on the thickness and material type of the thermoplastic substrate.

In some embodiments of the method, additional thermally stable layers, spacers, or any combination thereof may also be used. Spacers and additional thermally stable layers may be used for example to control the depth of embedment of the particles. These additional layers or spacers may also be used to ensure the thermoplastic element does not get damaged during pressing. For example, without a spacer the pressure of the pressing means may be high enough to reduce to the thickness of the thermoplastic element while it is at a temperature greater than or equal to its softening temperature.

In some embodiments, the donor sheet comprises metal, ceramic, plastic, or any combination thereof. In some embodiments, the donor sheet comprises polyimide. In some embodiments, the donor sheet is polyethylene terephthalate.

In some embodiments, the solvent is water. In some embodiments, the solvent is an organic solvent. In some embodiments, the organic solvent is selected from the group consisting of $C_1$-$C_4$ alcohol, $C_2$-$C_5$ ketone, $C_2$-$C_5$ ester, ether, and any combination thereof. In some embodiments, the solvent is selected from the group consisting of isopropanol, methanol, ethanol, cyclopentanone, n-butanol, methyl ethyl ketone, acetone, toluene, dichloromethane, hexane, propylene glycol methyl ether acetate, and any combination thereof. In some embodiments, the solvent is methanol or a 1:4 mixture of methanol:n-butanol.

In some embodiments, thermoplastic element is selected from the group consisting of acrylic, nylon, polyethylene, polypropylene, polystyrene, polyvinyl chloride, polycarbonate, polyethersulfone, polysulfone, polyether, polyester, polylactic acid, polyvinyl alcohol, polyvinyl butyral, ethylene vinyl acetate, ethylene tetrafluoroethylene, polytetrafluoroethylene, and combinations thereof.

In some embodiments, the pressing means applies a pressure of between about 10 to about 6000 pounds per square inch.

In some embodiments, the thermoplastic element is heated to a $T_{embed}$ between about 50 and about 300 degrees Celsius.

In some embodiments, the particles comprise a metal, or metal oxide material. In some embodiments, the particles comprise a photocatalytic compound. In some embodiments, the particles comprise a substance selected from doped or undoped titanium oxide, doped or undoped tungsten oxide, doped or undoped tin oxide, doped or undoped cerium oxide, doped or undoped copper oxide, doped or undoped silicon oxide, doped or undoped aluminium oxide, doped or undoped nickel oxide, and any combination thereof.

In some embodiments, the particles have a primary particle diameter less than 5 •m.

In some embodiments, the slurry is coated onto the donor sheet by spin coating, drop casting, roll coating, kiss roll coating, gravure coating, reverse coating, roll brush coating, spray coating, dip roll coating, bar coating, knife coating, and air knife coating. In some embodiments, the thickness of the coating is between 10 nm and 10 •m.

In some embodiments, the thickness of the donor sheet s from about 10 nm to about 10 mm.

In some embodiments, the thickness of the thermoplastic element is from about 10 nm to about 10 mm.

In some embodiments, the donor sheet is polyimide and thermoplastic element is polyethersulfone. In some embodiments, the thermoplastic element comprising polyethersulfone is heated to a $T_{embed}$ of between about 250 degrees Celsius to about 300 degrees Celsius. In some embodiments, sufficient pressure to embed the particles into the thermoplastic element is about 3000 psi.

In some embodiments, the donor sheet is polyethylene terephthalate and the thermoplastic substrate is ethylene vinyl acetate. In some embodiments, the thermoplastic substrate comprising ethylene vinyl acetate is heated to a $T_{embed}$ of between about 50 degrees Celsius and about 100 degrees Celsius.

For purposes of summarizing aspects of some embodiments and the advantages achieved over the related art, certain objects and advantages of some embodiments are described in this disclosure. Of course, it is to be understood that not necessarily all such objects or advantages may be achieved in accordance with any particular embodiment. Thus, for example, those skilled in the art will recognize that an embodiment may be embodied or carried out in a manner that achieves or optimizes one advantage or group of advantages as taught herein without necessarily achieving other objects or advantages as may be taught or suggested herein.

These and other embodiments are described in greater detail below.

Some embodiments include a method to embed particles into a thermoplastic element. In particular, the method is useful for embedding photocatalytic particles into a thermoplastic element. Photocatalytic particles can be used to provide sterilizable equipment made of thermoplastics. However, the methods of applying the particles to the thermoplastic surface are in need of improvement, and there remains a need for an inexpensive method that is useful for producing a broad range of stable particle embedded thermoplastic materials. Prior art methods have either required expensive equipment and are not scalable or they are limited in the types of thermoplastics and particles that can be used due to required exposure of a solvent to the thermoplastic. The method described herein involves the use of particles embedded in the surface of the thermoplastics which does not require the thermoplastic to be exposed to a solvent. The method allows for the particles to remain permanently within the thermoplastic substrate which prevents wear and deterioration of the particle properties. Photocatalytic particle properties include the ability to break down and rapidly deteriorate bacteria, algae, fungus, mold and mildew. In some embodiments, the method described herein, can therefore be used to manufacture a broad range of photocatalytic embedded thermoplastic materials that are useful for sterilizable equipment.

An inexpensive method to manufacture a particle embedded thermoplastic material is described herein, which does not require the exposure of the thermoplastic to a potentially damaging solvent. This novel method is described below.

First, a solvent and particles are mixed to form a slurry. Any suitable solvent can be used. In some embodiments, the donor sheet and the particles are substantially insoluble in the solvent. In some embodiments, the solvent is water. In some embodiments, the solvent is an organic solvent. In some embodiments, the organic solvent is selected from the group consisting of $C_1$-$C_4$ alcohol, $C_2$-$C_5$ ketone, $C_2$-$C_5$ ester, ether, and any combination thereof. In some embodiments, the solvent is selected from the group consisting of isopropanol, methanol, ethanol, cyclopentanone, n-butanol, methyl ethyl ketone, acetone, toluene, dichloromethane, hexane, propylene glycol methyl ether acetate, and any combination thereof. In some embodiments, the solvent is methanol or a 1:4 mixture of methanol:n-butanol. The particles may be more easily dispersed in one solvent versus another. A good dispersion of particles may be one in which the particles are not agglomerated and in which the particles do not settle down to the bottom of the slurry too quickly. It is important to choose a solvent in which the particles may be well dispersed because this will aid in forming a uniform coating of the particle in the thermoplastic material. In some embodiments the solvent is selected to provide a stable dispersion of the particles in the solvent. The particles may also breakdown, oxidize, or react in some way with certain solvents. Therefore an appropriate solvent must be chosen that does not compromise the integrity of the particles. In some embodiments, the solvent is chosen based on the desired chemical compatibility with the particles. In some embodiments, the solvent does not react in any way with the particles.

Once the slurry is formed, said slurry is then coated onto the surface of a donor sheet, wherein the donor sheet is thermally stable up to a temperature of at least $T_{embed}$. In some embodiments, the donor sheet is also chemically resistant to the solvent of choice. In some embodiments of the method, $T_{embed}$ equals or exceeds the Tg of the thermoplastic element but is equal to or less than the Tm of the thermoplastic element. In some embodiments, $T_{embed}$ is at or near the Tm of the thermoplastic. In some embodiments, $T_{embed}$ is within 100 degrees Celsius of the Tm of the thermoplastic element. In some embodiments, $T_{embed}$ is within 80 degrees Celsius of the Tm of the thermoplastic element. In some embodiments, $T_{embed}$ is within 60 degrees Celsius of the Tm of the thermoplastic element. In some embodiments, $T_{embed}$ is within 40 degrees Celsius of the Tm of the thermoplastic element. In some embodiments, $T_{embed}$ is within 30 degrees Celsius of the Tm of the thermoplastic element. In some embodiments, $T_{embed}$ is within 20 degrees Celsius of the Tm of the thermoplastic element. In some embodiments, $T_{embed}$ is within 10 degrees Celsius of the Tm of the thermoplastic element. In some embodiments, $T_{embed}$ is within 5 degrees Celsius of the Tm of the thermoplastic element. In some embodiments, $T_{embed}$ is between about 50 and about 300 degrees Celsius.

The donor sheet may be any suitable material. In some embodiments, the donor sheet comprises metal, ceramic, plastic, or any combination thereof. The donor sheet must be thermally stable up to a temperature of at least $T_{embed}$. As used herein "thermally stable" means the material does not decompose, melt, or otherwise breakdown when heat is applied up to a temperature of $T_{embed}$. Care must be taken to choose a donor sheet material that will not allow the particles to penetrate into the donor sheet material when the material is elevated to a temperature of $T_{embed}$ and pressure is applied. In some embodiments, the donor sheet material remains hard and rigid when elevated to at temperature of $T_{embed}$. It should be noted, for polymer materials, the Tg of the material may or may not be useful in determining the materials potential for use as a donor sheet. For example, the Tg of polyimide is assumed to be 360° C., however it remains thermally stable up to a temperature of 400° C. Therefore, polyimide is useful as a donor sheet for thermoplastic elements that require a $T_{embed}$ of up to about 380° C. In some embodiments, other polymer materials may also be chosen for use as a donor sheet based on their thermal stability at elevated temperature. Additionally, the donor sheet may also be chosen based on its ability to be removed from the thermoplastic element once the particles are embedded. Some materials may become adhered together and difficult to separate following the heating and pressure application. Therefore in may be desirable to choose a donor sheet material which can be easily separated from the thermoplastic element following the heat and pressure application. The donor sheet may also be chosen such that it can be easily coated by the slurry.

In general, most plastics can reasonably or completely resist at least some specific chemicals or solvents. Resistance means the plastic is completely unaffected and unaltered by contact with or exposure to the given chemical. For example, a poly(ethylene terephthalate) bottle is resistant to water and is stable to direct contact with water for an indefinite time period. The list of chemicals a plastic is resistant to is unique to each plastic and is dependent on the chemical structure of the plastic and the intrinsic physical properties thereof. In addition to chemical resistance, all thermoplastics by definition have a melting point (Tm), above which the polymer exists as a liquid at atmospheric pressure. However, there are plastics such as polyimide (Kapton) that do not dimensionally change or warp significantly at elevated temperatures. Kapton polyimide has no known solvents, does not melt, and is dimensionally stable up to 400° C. In some embodiments, the donor sheet comprises polyimide. Polyimide is a thermoset plastic that does not deform or decompose in temperatures up to 400° C., and is substantially insoluble in ethanol. It should be noted that thermoset polyimide remains thermally stable up to a temperature of 400° C. In some embodiments, the polyimide can be commercially available as Apical, Kapton, UPILEX, VTEC PI, Norton TH and/or Kaptrex polyimides from, inter alia, DuPont. In some embodiments, the polyimide can be poly(4,4'-oxydiphenylene-pyromellitimide). In some embodiments, the donor sheet comprises Kapton polyimide. In some embodiments, the donor sheet comprises polyethylene terephthalate (PET).

The thickness of the donor sheet may vary depending on the desired size of the particle embedded thermoplastic element. In some embodiments, the size of the pressing means and the heat source to heat the thermoplastic element will limit the size of the donor sheet that can be used. Also the type of material that is being used as the donor sheet may need to be considered when determining its size and thickness. Brittle materials which are easily broken may need to be thicker. In some embodiments, the thickness of the donor sheet is from about 10 nm to about 10 mm.

A variety of coating methods may be used to coat the slurry onto the donor sheet. In some embodiments, the method of coating the slurry onto the donor sheet may be appropriately selected from known methods used to coat liquid substances onto a solid substrate. Specific examples thereof include spin coating, drop casting, roll coating, kiss roll coating, gravure coating, reverse coating, roll brush coating, spray coating, dip roll coating, bar coating, knife coating, and air knife coating. In some embodiments, the slurry is coated onto the donor sheet by any one of the following methods: spin coating, drop casting, roll coating, kiss roll coating, gravure coating, reverse coating, roll brush coating, spray coating, dip roll coating, bar coating, knife coating, and air knife coating. In some embodiments, the thickness of the coating is between 10 nm and 1 mm. In some embodiments, the thickness of the coating is between 100 nm and 500 •m. In some embodiments, the thickness of the coating is between 1 •m and 300 •m. In some embodiments, the thickness of the coating is between 10 •m and 100 •m.

The uniformity and density of the particles embedded into the thermoplastic element may be controlled by the slurry composition and the coating process. A higher concentration of the particles in the slurry will allow a higher density of particles to be embedded into the thermoplastic element. Similarly, the dispersion properties of the slurry may determine the uniformity of the embedded particles on the thermoplastic element. Slurries with well dispersed particles, i.e. no agglomeration, may produce a more uniform surface of embedded particles on the thermoplastic element compared to slurries that are not well dispersed. In some embodiments, the concentration of particles in the slurry is optimized to produce the desired uniformity and density of particles embedded into the thermoplastic element. In some embodiments, the dispersion of the particles in the slurry is optimized to produce the desired uniformity and density of particles embedded into the thermoplastic element. Additionally, the coating process used to coat the slurry onto the donor sheet, and the conditions used in the coating process may also affect the uniformity and density of the embedded particles in the thermoplastic element. In some embodiments, the coating process is optimized to produce the desired uniformity and density of particles embedded into the thermoplastic element.

Once the donor sheet is coated with the slurry, the coated donor sheet is baked to evaporate substantially all of the solvent, leaving the particles loosely attached to the donor sheet. Standard methods known in the art can be used to evaporate the solvent. In some embodiments, the heating of the donor sheet is at a sufficient temperature and/or time to substantially remove all of the solvent without softening or deforming the donor sheet. The baking temperature and time may be chosen appropriately based on the solvent and the particles. In some embodiments, the solvent may evaporate at room temperature after a certain period of time, and therefore the baking temperature may be equal to room temperature. For example, highly volatile solvents such as ethanol or acetone, may not need to be baked at a temperature higher than room temperature as long as a suitable period of time is permitted to substantially evaporate all of said solvent. In some embodiments, the baking temperature may be 100 degrees Celsius, if for instance, the solvent is water. In some embodiments, the baking temperature is adjusted as needed based on the solvent used. In some embodiments, the baking time is adjusted as needed to evaporate substantially all of said solvent. Adjusting the pressure of the environment that the donor sheet is in can also be used to evaporate the solvent. For example, placing the donor sheet in a vacuum chamber at room temperature for a set period of time may be sufficient to evaporate substantially all of the solvent. In some embodiments, the pressure of the environment surrounding the donor sheet may be adjusted to evaporate the solvent. In some embodiments, the donor sheet is placed in an oven to evaporate the solvent. In some embodiments, the donor sheet may be placed on a hot plate to evaporate the solvent. In some embodiments, the donor sheet may be placed in a vacuum oven to evaporate the solvent. In some embodiments, the donor sheet may be left at room temperature and pressure for a sufficient period of time to evaporate substantially all of the solvent.

Once the solvent is evaporated from the donor sheet, the particles remain loosely attached to the donor sheet. As used herein, "loosely attached" means the particles are not covalently bonded, ionically bonded, or embedded into the donor sheet. In some embodiments, the adhesion strength of the particles to the donor sheet may be approximately 1B by the ATSM standard. In some embodiments, the loose attachment of the particles to the donor sheet occurs from attractive forces, including static, van der waals, or dipole-dipole. In some embodiments, the loose attachment of the particles to the donor sheet are from H-bonding. The loose attachment of the particles following evaporation of the solvent should be strong enough for the particles to remain attached and in their original placement when coated. In some embodiments, the strength of the loose attachment may not need to be enough to hold the particles in place if the surface of the donor sheet holding the particles is turned face down. In some embodiments of the method, the strength of the loose attachment must be high enough to hold the particles onto the donor sheet surface if it is turned face down. The donor sheet material may be chosen to optimize the strength of this attachment mechanism. In some embodiments, a ceramic or metal material may be used as a donor sheet which provides an electrostatic attachment mechanism between the particles and the donor sheet to help keep the particles attached to the donor sheet surface. In some embodiments a polymer or plastic material may be chosen as a donor sheet which provides a good enough attachment of the particles to allow for the donor sheet surface holding the particles to be placed facing down and the particles will not fall off. In some embodiments, a polyimide material is used as the donor sheet.

The adhesion strength of the loosely attached particles to the donor sheet can be measured by methods known in the art. In some embodiments, the adhesion strength of the loosely attached particles on the donor substrate may be quantified by application of a tape to the donor substrate surface holding the loosely attached particles, and then removing the tape and determining the percentage of particles that are removed from the donor substrate. In some embodiments, the amount which would be removed after the application of the tape could be greater than 65% (0B) (indicating the lowest adherence), about 35% to about 65% (1B), about 15% to about 35% (2B), about 5% to about 15%, less than 5%, from about 5% to substantially none removed (indicating the highest adherence) (5B). Those skilled in the art can recognize that a suitable method for assessing the adhesion, e.g., the removed percentage of the material on a substrate, can be by, but is not limited to, ASTM D3363.

The primary particle size of the particles may vary. In some embodiments, the particles have a primary particle diameter of less than 10 •m. In some embodiments, the particles have a primary particle diameter of less than 5 •m. In some embodiments, the particles have a primary particle diameter of less than 1 •m. In some embodiments, the particles have a primary particle diameter of less than 500 nm. In some embodiments, the required strength of the attachment mechanism holding the loosely attached particles to the donor sheet surface may limit the size of the particles that can be used. For example, it may be more difficult for larger particles to be loosely attached to the donor sheet surface without moving, especially if the donor sheet surface is required to face downward, while smaller particles may stick easily to the donor sheet surface without falling off if faced downward.

Once the solvent is removed from the donor sheet surface, the substantially dry donor sheet is contacted with a thermoplastic element, such that the donor sheet surface holding the loosely attached particles is in direct contact with the thermoplastic element. In some embodiments, the thermoplastic element is underneath the donor sheet, and the donor sheet surface holding the loosely attached particles is facing downward and is in direct contact with the top of the thermoplastic element. In some embodiments, the thermoplastic element is on top of the donor sheet, and the donor sheet surface holding the loosely attached particles is facing upward and is in direct contact with the bottom of the thermoplastic element. In some embodiments, the thermoplastic element and the donor sheet surface holding the loosely attached particles are pushed together side-by-side, such that the donor sheet surface holding the loosely attached particles is vertical.

In some embodiments, a certain portion of the particles may fall off of the donor sheet after the solvent is evaporated but prior to contacting the thermoplastic element. In some embodiments, the percentage of the loosely attached particles that fall off of the donor sheet after the solvent is evaporated and prior to contact with the thermoplastic element is between about 50-100%; between about 25-75%; between about 5-25%; between about 0.5-5%; and/or about 0%.

Once the donor sheet is in contact with the thermoplastic element, heat is applied to the thermoplastic element such that the temperature of the surface of the thermoplastic element that is in contact with the donor sheet reaches a temperature of $T_{embed}$, wherein $T_{embed}$ is the temperature at which the thermoplastic element is soft enough for embedment of the particles to occur.

Various thermoplastic materials may be used. In some embodiments, the thermoplastic element is selected from the group consisting of acrylic, nylon, polyethylene, polypropylene, polystyrene, polyvinyl chloride, polycarbonate, polyethersulfone (PES), polysulfone, polyether, polyester, polylactic acid, polyvinyl alcohol, polyvinyl butyral, ethylene vinyl acetate (EVA), ethylene tetrafluoroethylene (ETFE), polytetrafluoroethylene (PTFE), and combinations thereof. In some embodiments, the thermoplastic element comprises polytetrafluoroethylene (PTFE). In some embodiments, the thermoplastic element comprises PTFE commercially available as Teflon, from Du Pont). In some embodiments, the thermoplastic element comprises PES commercially available as Udel from Union Carbide. In some embodiments, the thermoplastic comprises ETFE commercially available as Tefzel. In some embodiments, the thermoplastic element comprises polycarbonate, PES, ETFE, EVA, and any combination thereof.

The $T_{embed}$ temperature that the thermoplastic material is heated up to depends on the material itself. All thermoplastics by definition have a melting point Tm, above which the polymer exists as a liquid at atmospheric pressure. Many thermoplastics also exhibit a glass transition temperature Tg (sometimes called a softening point), above which the polymer becomes increasingly soft or pliable with increasing temperature. In this method, heat is applied to the thermoplastic element such that the temperature of the thermoplastic element reaches a point at which the thermoplastic element is soft enough for the particles to be embedded into it, given the pressure that will be applied. In some embodiments, $T_{embed}$ equals or exceeds the Tg of the thermoplastic element but is equal to or less than the Tm of the thermoplastic element. In some embodiments, $T_{embed}$ is at or near the Tm of the thermoplastic. In some embodiments, $T_{embed}$ is within 100 degrees Celsius of the Tm of the thermoplastic element. In some embodiments, $T_{embed}$ is within 80 degrees Celsius of the Tm of the thermoplastic element. In some embodiments, $T_{embed}$ is within 60 degrees Celsius of the Tm of the thermoplastic element. In some embodiments, $T_{embed}$ is within 40 degrees Celsius of the Tm of the thermoplastic element. In some embodiments, $T_{embed}$ is within 30 degrees Celsius of the Tm of the thermoplastic element. In some embodiments, $T_{embed}$ is within 20 degrees Celsius of the Tm of the thermoplastic element. In some embodiments, $T_{embed}$ is within 10 degrees Celsius of the Tm of the thermoplastic element. In some embodiments, $T_{embed}$ is within 5 degrees Celsius of the Tm of the thermoplastic element. In some embodiments, $T_{embed}$ is between about 50 and about 300 degrees Celsius.

Several methods may be used to apply heat to the thermoplastic element. In some embodiments, the donor sheet and the thermoplastic element may be placed into an oven, wherein all components are heated together in the oven and the pressure is also applied while the components are in the oven. In some embodiments, a hot plate may be used, wherein the thermoplastic element is placed on top of a hot plate, and the hot plate is set to the desired temperature. In some embodiments, a heated pressing means may be used to supply the heat to the thermoplastic element. Other methods of heating, which are known in the art, may also be used to apply heat to the thermoplastic element.

Once the thermoplastic element reaches the desired $T_{embed}$ temperature, a sufficient pressure is applied to embed the particles into the thermoplastic element. When the thermoplastic element temperature is elevated equal to or greater than its softening temperature, the material becomes soft and pliable, allowing the particles on the donor sheet surface, to be pressed into, and embed into the softened surface of the thermoplastic element. The pressure that is required to embed the particles into the thermoplastic element should be optimized appropriately based on the materials that are being used and the processing conditions. In some embodiments, the sufficient pressure applied is between about 10 to about 6000 pounds per square inch.

It may be desirable to use a heated pressing means to simultaneously apply heat to the thermoplastic element while also applying sufficient pressure to embed the particles into the thermoplastic element. In some embodiments of the method, a heated pressing means is used to simultaneously heat and press the stack together. In some embodiments, the temperature of the heated pressing means, the pressure applied by the heated pressing means, and the length of time the thermoplastic element and donor sheet are heated and pressed together by the heated pressing means, are variables that can be optimized based on the thickness and material type of the thermoplastic element. Since the heat is applied to the thermoplastic element on the opposite side of where it is in direct contact with the donor sheet surface, the exposure time of the thermoplastic element to the heat source will need to be adjusted based on the thickness of the thermoplastic element. Thermoplastic elements that are thicker will require exposure to the heat source for a longer period of time in order for the thermoplastic element surface in contact with the donor sheet to reach the desired softening temperature, $T_{embed}$. In some embodiments, a thermoplastic element that is 254 m thick is exposed to a heated pressing means for 1 minute to reach the desired temperature.

In some embodiments, the donor sheet is polyimide and thermoplastic element is polyethersulfone. In some embodiments, the thermoplastic element comprising polyethersulfone is heated to a $T_{embed}$ of between about 250 degrees Celsius to about 300 degrees Celsius. In some embodiments, sufficient pressure to embed the particles into the thermoplastic element is about 3000 psi.

In some embodiments, the donor sheet is polyethylene terephthalate and the thermoplastic substrate is ethylene vinyl acetate. In some embodiments, the thermoplastic substrate comprising ethylene vinyl acetate is heated to a $T_{embed}$ of between about 50 degrees Celsius and about 100 degrees Celsius.

Once the particles are embedded into the thermoplastic element, the thermoplastic element is allowed to cool so that the thermoplastic element returns to its hard and rigid state, with the particles permanently embedded into the surface of the thermoplastic element. The cooling of the thermoplastic element can be accomplished by simply turning off or removing the heat source. Other standard methods known in the art may also be used, such as placing the thermoplastic element into a refrigerator. However, care must be taken when handling the thermoplastic element before it has cooled as it may be easily damaged in this softened state. In some embodiments, the thermoplastic element is cooled by turning off the heat source and allowing it to return to room temperature.

Once the thermoplastic element has returned to room temperature it is separated from the donor sheet, and the particles remain permanently embedded in the thermoplastic element, providing a particle embedded thermoplastic element.

In some embodiments of the method, additional thermally stable layers, spacers, or any combination thereof may also be used. Spacers and additional thermally stable layers may to used for example to control the depth of embedment of the particles. These additional layers or spacers may also be used to ensure the thermoplastic element does not get damaged during pressing. For example, without a spacer the pressure of the pressing means may be high enough to reduce to the thickness of the thermoplastic substrate while it is at $T_{embed}$, which is a temperature greater than or equal to its softening temperature.

In some embodiments, a metal oxide particle is used. In some embodiments, a metal oxide nanoparticle is used. In some embodiments, the metal oxide nanoparticle comprises a photocatalytic compound. Photocatalysts are well known to those skilled in the art as substances that help bring about a light-catalyzed reaction and function to decompose, kill, deodorize and inhibit the growth of nuisance organisms. A variety of photocatalysts may be used. A suitable photocatalytic compound can be doped or undoped $TiO_x$, doped or undoped $WO_x$, doped or undoped $SnO_x$, doped or undoped $CeO_x$, or any combination thereof. In some embodiments, the doped TiOx compound can be $TiSn(CNO)_x$ as described in U.S. patent application Ser. No. 13/741,191, filed Jan. 14, 2013 (United States Publication No. 2013/0192976, published Aug. 1, 2013) which is incorporated by reference in its entirety. In some embodiments, the photocatalytic compound can be a $Cu_xO$ loaded photocatalytic composite as described in U.S. patent application Ser. No. 13/840,859, filed Mar. 15, 2013; and/or U.S. Provisional Application 61/835,399, filed Jun. 14, 2013, which are incorporated by reference in their entirety. Photocatalytic particles are often in powder form. In some embodiments, the photocatalytic particles are in powder form.

In addition, the above-mentioned photocatalyst and co-catalyst can also be used as the particles in some embodiments.

In some embodiments, the method comprises applying sufficient heat to closely approach or exceed Tm of the thermoplastic element but remain below the decomposition temperature of the donor sheet to predispose the thermoplastic element to receive the particles from the donor sheet. The heat is sufficient to soften the thermoplastic element such that the particles can be embedded into the surface of the thermoplastic element. Considerations for determining the heating level, $T_{embed}$, include the particular donor sheet material and its respective softening characteristics or parameters. For example, if the donor material is polyimide and the recipient material is polyether sulfone (PES), then the temperature, $T_{embed}$, to be applied can be between 240° C. to about 280° C. This temperature range exceeds the Tg of PES, which is at about 185° C., but remains below the deformation temperature of a polyimide sheet, e.g., greater than 400° C. In another example, if the donor sheet is PET and the thermoplastic element comprises ethylene vinyl acetate (EVA), then the temperature to be applied can be between 50° C. to about 100° C., e.g., about 80° C. This temperature range exceeds the Tg of EVA, which begins at about −15° C., but remains below the deformation temperature of a PET sheet, e.g., greater than 120° C. In some embodiments, the donor sheet comprises polyimide, the thermoplastic element is PES and the solvent is methanol, and wherein the donor sheet is heated to about 250° C. to about 300° C. In some embodiments, sufficient pressure to embed the nanoparticles into the thermoplastic is about 3000 psi. In some embodiments, the donor sheet comprises PET, the thermoplastic element is EVA and the solvent is methanol, and wherein the thermoplastic element is heated to about 50° C. to about 100° C.

In some embodiments, the method can comprise applying sufficient pressure to the stacked donor and thermoplastic element to embed the nanoparticles into the thermoplastic element. The pressure is sufficient to embed the nanoparticle materials into the softened thermoplastic element such that the nanoparticles can be inserted into the surface of the thermoplastic element. Considerations for determining the pressure level include the particular donor material, the thermoplastic material, their respective softening characteristics or parameters, the time of application and the temperature being applied. For example, if the donor material is polyimide and the thermoplastic material is PES, then the pressure to be applied can be between 10 pounds per square inch (PSI) to about 6000 pounds per square inch (PSI). In another example, if the donor material is PET, the thermoplastic material is EVA, and the temperature $T_{embed}$ being applied is between 50° C. to about 100° C., then a suitable pressure can be about 3000 PSI. In another example, if the donor material is polyimide, the thermoplastic material is polycarbonate and the temperature $T_{embed}$ being applied is between 200° C. to about 270° C., then a suitable pressure can be between about 10 PSI and about 6000 PSI. In another example, if the donor material is polyimide, the recipient material is ETFE and the temperature $T_{embed}$ being applied is between 200° C. to about 270° C., then a suitable pressure can be between about 10 PSI and about 6000 PSI.

Figure 9:
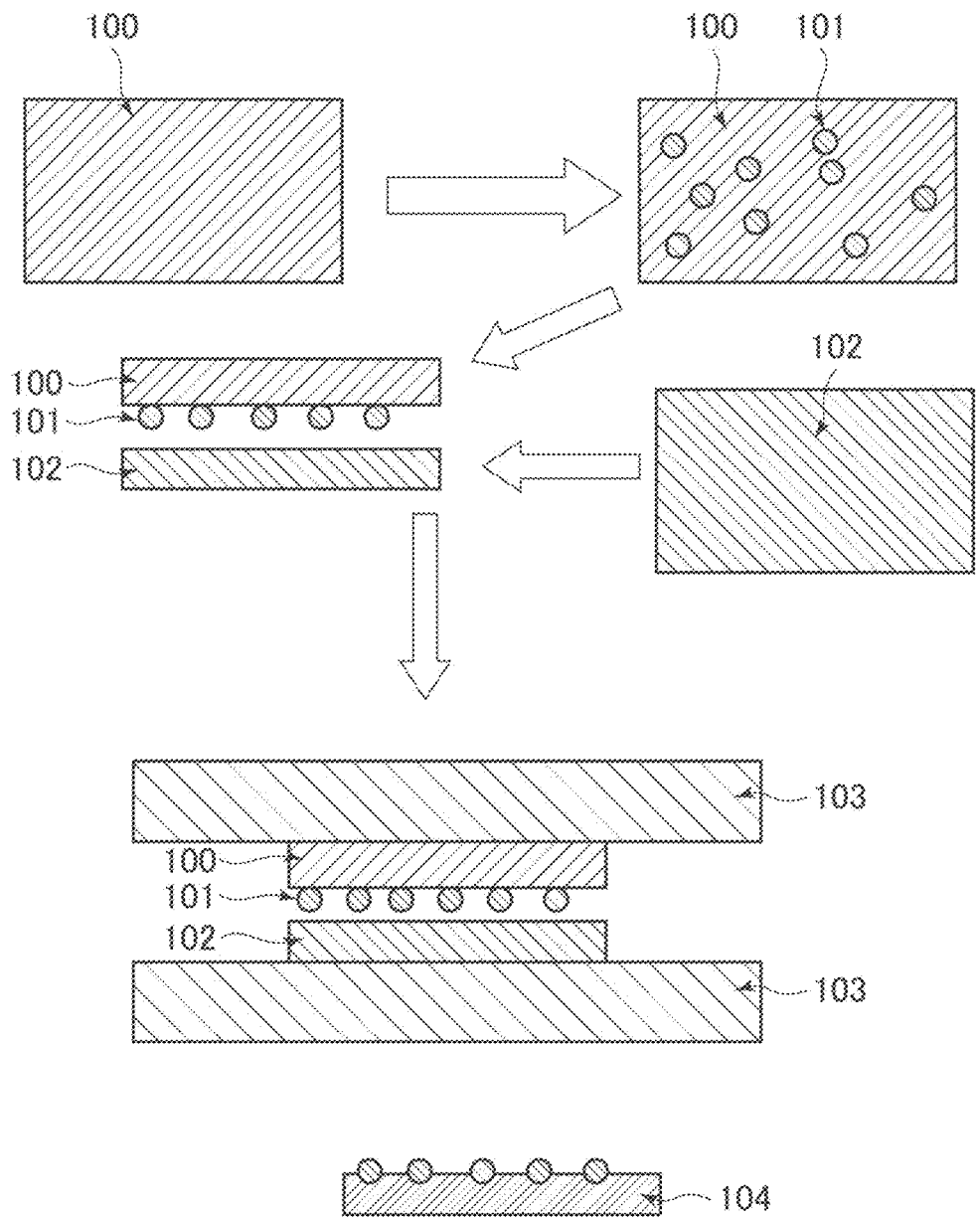
FIG. 9 illustrates an embodiment of the method of embedding particles into a thermoplastic element.

In some embodiments, a method of embedding particles into a thermoplastic element is illustrated in FIG. 9 wherein the method comprises the steps of coating a donor sheet 100 with a slurry comprising a solvent and particles 101, wherein the donor sheet material is thermally stable up to a temperature of at least $T_{embed}$, wherein the donor sheet material and particles are substantially insoluble in the slurry solvent, then baking the donor sheet to evaporate substantially all of the solvent, leaving the particles loosely attached to the donor sheet, then contacting the substantially dry donor sheet with a thermoplastic element 102, wherein the surface of the donor sheet comprising the loosely attached particles is in direct contact with the thermoplastic element, then applying sufficient heat to reach a temperature of $T_{embed}$, wherein $T_{embed}$ is the temperature at which the thermoplastic element is soft enough for embedment of the particles to occur, then applying sufficient pressure to embed the particles into the thermoplastic element, wherein the heat and pressure are supplied by a heated pressing plate 103, then cooling the particle embedded thermoplastic element 104, and separating the particle embedded thermoplastic element from the donor sheet.

Figure 10:
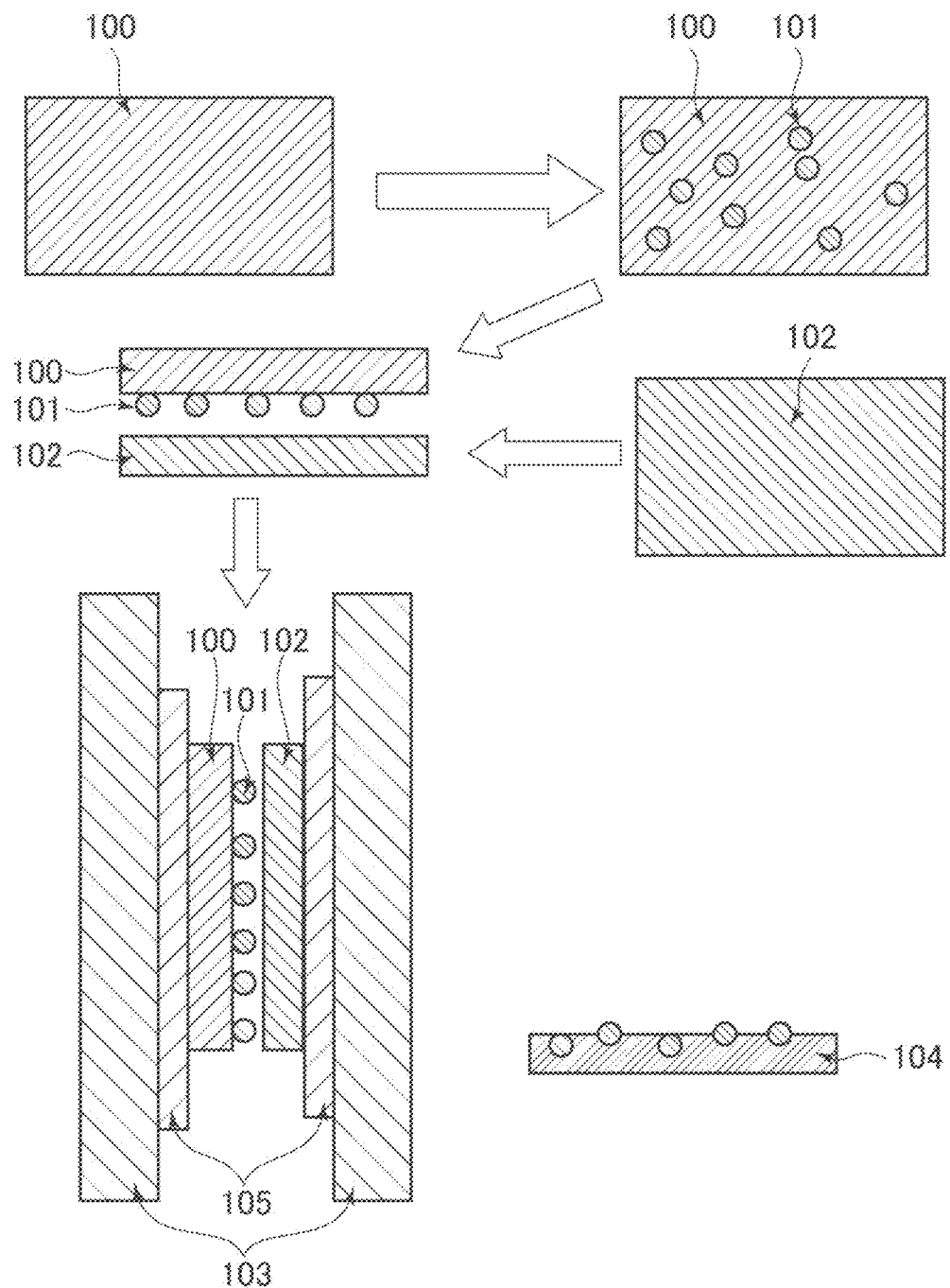
FIG. 10 illustrates an embodiment of the method of embedding particles into a thermoplastic element.

In some embodiments, a method of embedding particles into a thermoplastic element is illustrated in FIG. 10 wherein the method comprises the steps of coating a donor sheet 100 with a slurry comprising a solvent and particles 101, wherein the donor sheet material is thermally stable up to a temperature of at least $T_{embed}$, wherein the donor sheet material and particles are substantially insoluble in the slurry solvent, then baking the donor sheet to evaporate substantially all of the solvent, leaving the particles loosely attached to the donor sheet, then contacting the substantially dry donor sheet with a thermoplastic element 102, wherein the surface of the donor sheet comprising the loosely attached particles is in direct contact with the thermoplastic element, then applying sufficient heat to reach a temperature of $T_{embed}$, wherein $T_{embed}$ is the temperature at which the thermoplastic element is soft enough for embedment of the particles to occur, then applying sufficient pressure to embed the particles into the thermoplastic element, wherein the heat and pressure are supplied by a heated pressing plate 103 and additional thermally stable sheets 105 are used in the heated pressing plate, then cooling the particle embedded thermoplastic element 104, and separating the particle embedded thermoplastic element from the donor sheet.

In some embodiments, a method of embedding particles into a thermoplastic element is illustrated in FIG. 11 wherein the method comprises the steps of coating a donor sheet 100 with a slurry comprising a solvent and particles 101, wherein the donor sheet material is thermally stable up to a temperature of at least $T_{embed}$, wherein the donor sheet material and particles are substantially insoluble in the slurry solvent, then baking the donor sheet to evaporate substantially all of the solvent, leaving the particles loosely attached to the donor sheet, then contacting the substantially dry donor sheet with a thermoplastic element 102, wherein the surface of the donor sheet comprising the loosely attached particles is in direct contact with the thermoplastic element, then applying sufficient heat to reach a temperature of $T_{embed}$, wherein $T_{embed}$ is the temperature at which the thermoplastic element is soft enough for embedment of the particles to occur, then applying sufficient pressure to embed the particles into the thermoplastic element, wherein the heat and pressure are supplied by a heated pressing plate 103 and additional thermally stable sheets 105 and spacers 106 are used in the heated pressing plate, then cooling the particle embedded thermoplastic element 104, and separating the particle embedded thermoplastic element from the donor sheet.

Next, the embodiments relating to the above-mentioned "Method C" are described below.

Visible light activated photocatalysts can be deployed for self-cleaning, air and water purification and many other interesting applications usually without any post-deployment non-renewable energy costs. This is because the photocatalysts are able to decompose pollutants (like dyes, volatile organic compounds and NOx) using light available in the ambient like solar radiation or indoor and outdoor lighting. With the anticipated rapid adoption of UV-free indoor lighting (like LEDs and OLEDs), it is imperative to find ways to deploy visible-light activated photocatalysts in indoor applications for instance in cleaning room air in domestic, public and commercial spaces especially in confined areas like aircraft, public buildings, etc. Moreover, additional applications for antibacterial surfaces and self-cleaning materials can have wide applicability in the food service, transportation, health care and hospitality sectors.

Various methods have been proposed to fix titanium oxide. See, for example, U.S. Pat. Nos. 5,897,958; 6,228, 480; 6,407,033; 7,510,595 and Reissued U.S. Pat. No. RE38,850. Thus there is a need for affixation of titanium oxide to substrate surfaces.

In some embodiments, a method for creating a photocatalytic surface on a photocatalytic element is described, the method comprising providing a photocatalytic element with a surface, the element comprising photocatalytic nanoparticles and a photodegradable polymeric matrix, at least a portion of the photocatalytic nanoparticles adjacent the surface of the polymer matrix surface and covered by the polymeric matrix; and irradiating the surface of the polymer matrix a sufficient amount to expose at least some photocatalytic nanoparticles. In some embodiments, the thickness of polymeric matrix decomposed is less than about 100 nm. In some embodiments, the amount of radiant energy is at least about 40 $W/m^2$ for at least about 0.25 hour. In some embodiments, the polymeric matrix comprises a urethane polymer. In some embodiments, the urethane polymer comprises a urethane acrylate polymer. In some embodiments, the sufficient amount of radiant energy comprises at least about 50 $KJ/m^2$.

These and other embodiments are described in greater detail below.

In some embodiments, a method for creating, modifying and/or improving a photocatalytic surface on a photocatalytic element can be provided, the method comprising providing a photocatalytic element with a surface, the element comprising a photocatalytic composition and a photodegradable polymeric matrix, and photoetching the surface by irradiating the element with a sufficient amount of radiant energy to decompose an amount of polymeric matrix, exposing additional photocatalytic composition on the surface. By decomposing is meant an amount of the polymeric matrix material is removed from the initial polymeric layer. In some embodiments, the amount and/or thickness of polymeric matrix decomposed can be less than about 100 nm. In some embodiments, the amount of polymeric matrix decomposed is about 10% of the total initial thickness. In some embodiments, the amount of radiant energy is at least about 40 $W/m^2$, at least 50 $W/m^2$, and/or at least 60 $W/m^2$ for at least about 5 minutes, 10 minutes, 15 minutes, 30 minutes, 45 minutes, 1 hour, 2 hour, 3 hour, and/or 4 hour (light meter readings at the surface of the strips). In some embodiments, the amount of radiant energy applied can be at least about 1.0 $J/cm^2$, 2.5 $J/cm^2$, 5.0 $J/cm^2$, 7.5 $J/cm^2$, 10.0 $J/cm^2$, 20 $J/cm^2$, to less than about 90.0 $J/cm^2$, 85.0 $J/cm^2$, 80.0 $J/cm^2$, 75.0 $J/cm^2$, 70.0 $J/cm^2$, 65.0 $J/cm^2$, 60.0 $J/cm^2$, and/or 50 $J/cm^2$, or any combination of the aforementioned values. In some embodiments, the polymeric material comprises a urethane polymer. In some embodiments, the urethane polymer comprises a urethane acrylate polymer. In some embodiments, the sufficient amount of radiant energy comprises at least about 60 $W/m^2$ for at least about 15 minutes.

Figure 12A:
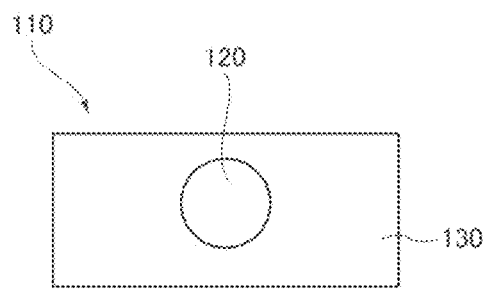
FIG. 12A is a cross-sectional view of a photocatalytic element prior to photo etching.
Figure 12B:
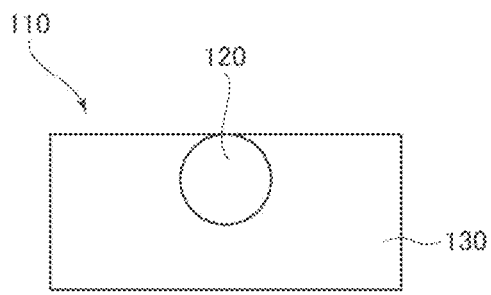
FIG. 12B is a cross-sectional view of a photocatalytic element prior to photo etching.
Figure 12C:
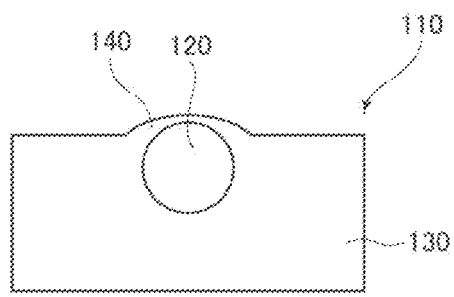
FIG. 12C is a cross-sectional view of a photocatalytic element prior to photo etching.

FIGS. 12A-12C show cross-sections of photocatalytic elements 110 having a photocatalytic material 120, for example photocatalytic nanoparticle, disposed within a photodegradable polymeric matrix 130. FIG. 12A shows photocatalytic material disposed below the surface of the polymeric matrix 130. FIG. 12B shows photocatalytic material disposed partially below the surface of the polymeric matrix 130. The elements 110 have a pre-exposure surface. In some embodiments, as shown in FIG. 12C, the surface of the element 110 may be disposed upward, having a bubble or thin layer 140 of polymer matrix material 130 distended or bulging upward.

Figure 13A:
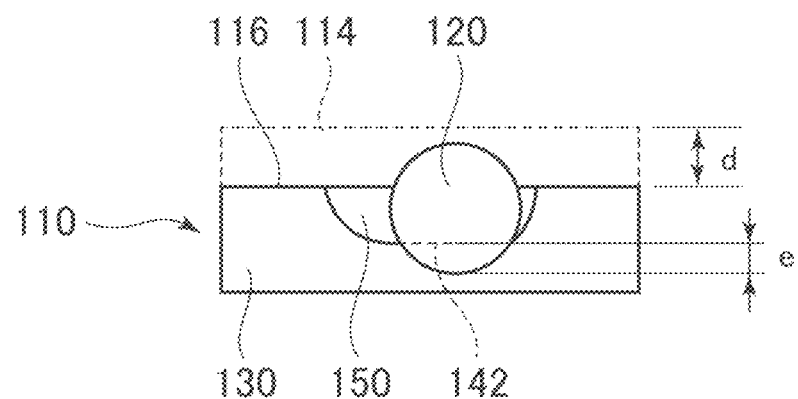
FIG. 13A is a cross-sectional view of a photocatalytic element post photo etching.
Figure 13B:
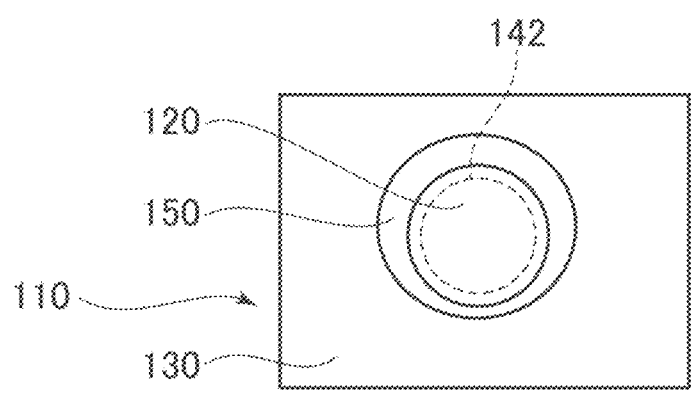
FIG. 13B is a top view of a photocatalytic element post photo etching.
Figure 14A:
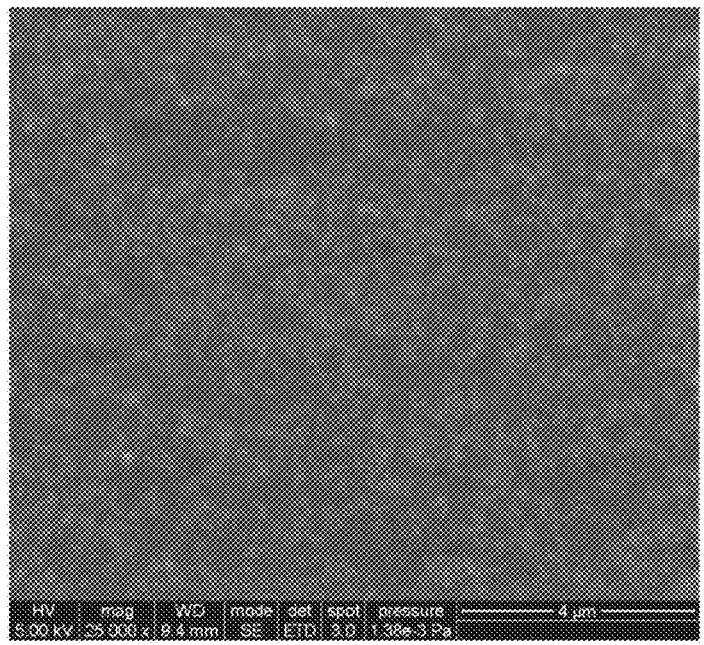
FIG. 14A is an scanning electron microscope image of a surface of an embodiment made as described in Example 1.
Figure 14B:
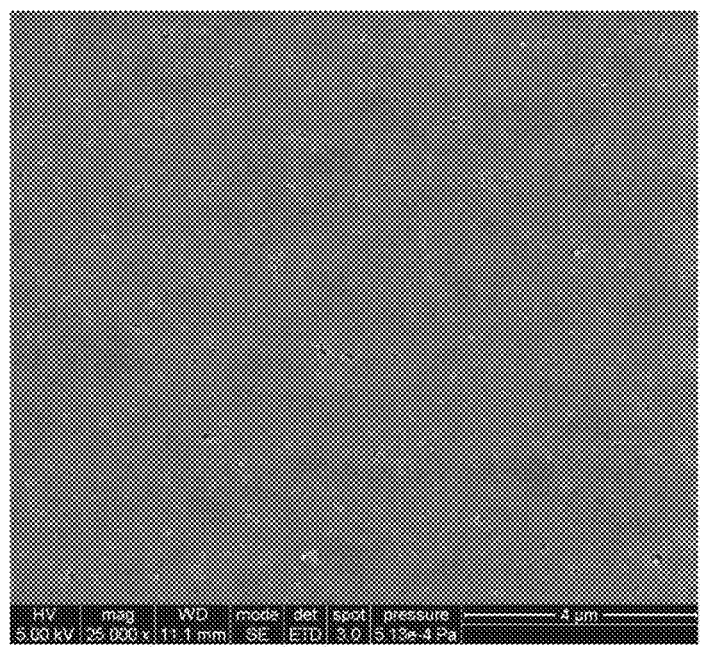
FIG. 14B is an scanning electron microscope image of a surface of an embodiment made as described in Example 5.
Figure 14C:
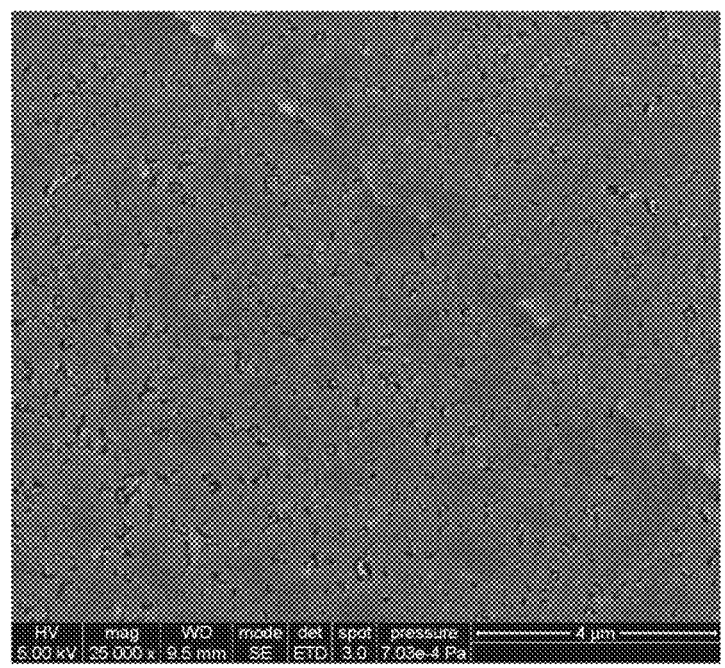
FIG. 14C is an scanning electron microscope image of a surface of an embodiment made as described in Example 6.

FIGS. 13A and 13B show a photocatalytic element 110 after the photodegradation and/or photoetching method[s] described herein. A photocatalytic material 120, for example a nanoparticle, can be disposed within the photodegraded polymeric matrix 130. Irradiating the surface 114 of the polymer matrix 130 a sufficient amount, exposes at least a portion of some of the photocatalytic nanoparticles 120. The initial surface 114 of the polymeric matrix 130 can be decomposed a portion or amount "d" to a second surface level 116. In some embodiments, the amount of decomposition "d" can be sufficient to expose the nanoparticle 120, yet retain the nanoparticle within the matrix 130. In some embodiments, the amount d can be the vertical thickness of the polymeric matrix that can be decomposed and/or eroded. In some embodiments, the amount d can be less than about 100 nm. In some embodiments, the amount can be less than 90 nm, less than 80 nm, less than 70 nm, less than 60 nm, less than 50 nm. In some embodiments, the amount d can be less than about 10%, less than 20%, less than about 30%, and/or less than about 40% of the total thickness of the matrix 130. In some embodiments, the amount of decomposition "d" is sufficient to expose the nanoparticle 120, yet retain the nanoparticle within the matrix 130. For example, in some embodiments, a distance "e", the difference between the depth of the annular cavity and the bottom of the nanoparticle, is greater than 0 nm, at least about 5 nm, at least about 7 nm, at least about 10 nm. In some embodiments, the amount d is less than about 100 nm.

In some embodiments, an annular void 150 can be defined in part by and adjacent the nanoparticles and the photodegradable polymeric matrix. In some embodiments, the width of the annular void can be about 5 nm, about 10 nm, about 15 nm, about 20 nm, about 30 nm, and or about 40 nm. In some embodiments, the depth of the annular void can be about 5 nm, about 10 nm, about 15 nm, about 20 nm, about 30 nm, and or about 40 nm. In some embodiments, at least a portion or amount "e" of the photocatalytic matrix retains the photocatalytic material 120 therein. The "e" can be the difference between the depth of the annular void and the depth of the nanoparticle below the surface 116.

In some embodiments, a method for increasing the photocatalytic activity of a photocatalytic element is provided. In some embodiments, the increase in photocatalytic activity can result from increased exposure of photocatalytic composition on the surface of the photocatalytic element. In some embodiments, the photocatalytic element can comprise a photocatalytic composition and a photodegradable polymeric matrix, at least a portion of the photocatalytic composition, e.g., photocatalytic nanoparticle, adjacent the surface of the polymer matrix surface and covered by the polymer matrix. In some embodiments, the photocatalytic composition can be disposed on the surface of the element. In some embodiments, the photocatalytic composition can be embedded in and disposed throughout the photocatalytic element. In some embodiments, the photocatalytic composition may not be present on the surface of the photocatalytic element prior to treatment by the described method. Photocatalytic activity can be increased by increasing the amount of photocatalytic composition exposed on the surface of the photocatalytic element. The photodegradable polymeric matrix can be eroded by exposure to electromagnetic radiation, thereby exposing more of the photocatalytic composition embedded therein.

In some embodiments, the method can include providing a photocatalytic element with a surface, the element comprising photocatalytic nanoparticles and a photodegradable polymeric matrix, at least a portion of the photocatalytic nanoparticles adjacent the surface of the polymer matrix surface and covered by the polymeric matrix. In some embodiments, providing the photocatalytic element can include mixing a polymeric binder with a first organic solvent to create a polymeric solution. In some embodiments, providing the photocatalytic element can include mixing a dispersing agent with the organic binder and a first organic solvent. In some embodiments, the photocatalytic material is mixed with the polymeric solution. In some embodiments, the photocatalytic material is suspended in a second organic solvent to create a photocatalytic suspension. In some embodiments, the second organic solvent is the same as the first organic solvent. In some embodiments, the second organic solvent is different from the first organic solvent.

The photocatalytic element can comprise a photocatalytic composition. In some embodiments, the photocatalytic composition can be disposed throughout the photocatalytic element. In some embodiments, the photocatalytic composition can be an oxide comprising an element that can be titanium, tungsten, tantalum, tin, zinc or strontium oxide. In some embodiments, the oxide can be doped or undoped, loaded or unloaded. In some embodiments, the oxide can have a valence band deeper than that of the copper loaded materials valence bands. In some embodiments, the photocatalytic composition can be a plural phase composite of photocatalytic compositions. In some embodiments, the photocatalytic composition can be ananatase, rutile, wurtzite, spinel, perovskite, pyrochlore, garnet, zircon and/or tialite phase material or mixtures thereof. Each of these options is given its ordinary meaning as understood by one having ordinary skill in the semiconductor art. Comparison of an x-ray diffraction pattern of a given standard and the produced sample is one of a number of methods that may be used to determine whether the sample comprises a particular phase. Exemplary standards include those XRD spectra provided by the National Institute of Standards and Technology (NIST) (Gaitherburg, Md., USA) and/or the International Centre for Diffraction Data (ICDD, formerly the Joint Committee on Powder Diffraction Standards [JCPDS]) (Newtown Square, Pa., USA).

In some embodiments, the plural phase photocatalytic compositions comprise anatase phase and rutile phase compounds. In some embodiments, the plural phase photocatalytic materials can be titanium oxides. In some embodiments, the anatase phase can be 2.5% to about 97.5%, 5% to about 95%, and/or about 10% to about 90%; and the rutile phase can be 97.5% to about 2.5%, 95% to about 5%, and/or about 10% to about 90%. A non-limiting example of a suitable material includes, to a $TiO_2$ mixture sold under the brand name P25 (83% Anataste $TiO_2$+17% Rutile $TiO_2$) sold by Evonik (Parissipany, N.J., USA)).

In some embodiments, the photocatalytic compositions can comprise nanoparticles. In some embodiments, the photocatalytic compositions comprise compounds having an average particle diameter of between about 10-100 nm. In some embodiments, the average particle diameter can be between about 20 nm to about 60 nm.

In some embodiments, the photocatalytic material can be a $Cu_xO$ loaded photocatalytic composite as described in U.S. patent application Ser. No. 13/840,859, filed Mar. 15, 2013; and/or U.S. Provisional Application 61/835,399, filed Jun. 14, 2013; and U.S. patent application Ser. No. 13/741,191, filed Jan. 14, 2013 (United States Publication No. 2013/0192976, published Aug. 1, 2013).

In addition, the above-mentioned photocatalyst and co-catalyst can also be used as the photocatalytic nanoparticles in some embodiments.

In some embodiments, the photocatalytic compositions can comprise a binder material. In some embodiments, the binder material can be a can be a UV curable resin. In some embodiments, the UV curable resin is a urethane resin. In some embodiments, the urethane resin is a urethane acrylate resin. In some embodiments, the urethane acrylate resin comprises at least 2, at least 3, and/or at least 5 acryloyl groups per repeating group. In some embodiments, the suitable urethane resins can be commercially available products, e.g., UNIDIC 17806 (80% by mass of the non-volatile content; polyfunctional urethane acrylate by DIC International (USA), LLC, Parsippany, N.J., USA); Ebecryl 8701, Ebecryl8301, Ebecryl8405 (Allnex USA, Smyrna, Ga., USA/Cytec Industries, Inc., Woodland, N.J., USA)), OC-3021, OC-4021, OC-4122 (Dymax Oligomers and Coatings, Torrington, Conn., USA); HC-5619 (Addison Clearwave Coatings, Inc., St. Charles, Ill., USA); and Silfort UVHC3000 (Momentive Performance Materials, Inc., Albany, N.Y., USA).

In some embodiments, the composition can further include a photo-initiator. In some embodiments, the photo-initiator can be a can be a free radical photoinitiator. In some embodiments, the photoinitiator can be an alpha amino ketone, a bis acyl phosphine (BAPO), an alpha hydroxyl ketone and/or combinations and/or mixtures thereof. In some embodiments, the suitable photoinitiator can be 2-methyl-1-[4-(methylthio)phenyl]-2-(4-morpholinyl)-1-propanone (Irgacure 907, BASF Corp., Florham, N.J., USA), phosphine oxide (phenyl bis(2,4,6-trimethyl benzoyl) [Irgacure 819]), and/or 2-hydroxy-2-methyl-1-phenyl-1-propanone [darocur 1173]. In some embodiments, the suitable photoinitiator can be commercially available products, e.g., Irgacure 907, Irgacure 2022 (20 wt % Irgacure 819/80% Darocur 1173]).

In some embodiments, the binder can be dissolved in an organic solvent. In some embodiments, the photocatalytic material is substantially insoluble in the organic solvent. In some embodiments, the organic solvent can be, for example, a hydrocarbon, ketone, ester, ether or alcohol.

Examples of the above hydrocarbon include toluene and xylene; examples of the above ketone include methyl ethyl ketone, methyl isobutyl ketone, methyl n-amylketone, diethyl ketone and cyclohexanone; examples of the above ester include ethyl acetate, n-butyl acetate, i-amyl acetate, propylene glycol monomethyl ether acetate, 3-methoxybutyl acetate and ethyl lactate; examples of the above ether include ethylene glycol dimethyl ether, ethylene glycol diethyl ether, tetrahydrofuran and dioxane; and examples of the above alcohol include 1-hexanol, 4-methyl-2-pentanol, ethylene glycol monomethyl ether, ethylene glycol monoethyl ether, ethylene glycol mono-n-propyl ether, ethylene glycol mono-n-butyl ether, propylene glycol monomethyl ether, propylene glycol monoethyl ether and propylene glycol mono-n-propyl ether. In some embodiments, the organic solvent can be a $C_1$-$C_7$ alcohol. In some embodiments, the organic solvent can be a $C_1$-$C_7$ ketone. In some embodiments, the organic solvent can be cyclopentanone, propylene glycol monomethyl ether acetate (PGMEA), N-methylpyrrolidone (NMP), methyl ethyl ketone (MEK), toluene, ethyl acetate and/or butyl acetate. In some embodiments, providing the binder and photocatalytic material suspension further comprises dissolving a urethane resin in a cyclopentanone solvent. These organic solvents may be used alone or in combination of two or more.

In some embodiments, providing the photocatalytic element can include mixing a dispersing agent with the organic binder and a first organic solvent. In some embodiments, the dispersing agent can be cationic, anionic, and/or non-ionic. In some embodiments, the dispersing agent can be Additol xl 203 (Silicone-containing cationic dispersing agent) (Allnex USA, Smyrna, Ga., USA), Additol xl 251 (Acidic, anionic dispersing agent), Additol xl 6208/60 (Polymeric non-ionic dispersing agent), Flowen G700 (polycarboxylic acid-based, molecular weight $M_w$=230) (Kyoeisha Chemical Co., LTD, Osaka, JP) and/or mixtures or combinations thereof.

In some embodiments, the photocatalytic/binder material (photocatalytic material/binder suspension) can be applied to a substrate providing a coated surface. In some embodiments the substrate can be a thermoplastic polymer. In some embodiments, the substrate can be a thermosetting polymer. In some embodiments, the substrate can be any of polyethelene, polypropylene, polyester, polystyrene, polyamide, polyimide, polysulfone, polyethersulfone (PES), polyacrylate, polkyacrylonitrile, polycarbonate (PC), polymethyl methacrylate (PMMA), polyvinylchloride (PVC) and for mixtures thereof. In some embodiments, the substrate can comprise a polyester. In some embodiments, the polyester can be, for example, polyethylene terephthalate (PET), polybutylene terephthalate (PBT), polyethylene naphthalate (PEN).

In some embodiments, the method includes photoetching the coated surface by irradiating the element with a sufficient amount of radiant energy to decompose an amount of polymeric matrix, exposing additional photocatalytic composition on the surface. While not wanting to be limited by theory, it is believed that continued irradiation beyond a certain amount of time could result in an undesired amount of photocatalytic nanoparticle[s] being released from the polymer matrix surface. Thus in some embodiments, there can be a desired amount/time of irradiating to effect the desire amount of photoetching.

In order to enhance the photocatalytic effect of the element, the surface of the photocatalytic element can be modified and/or degraded by electromagnetic radiation. In some embodiments, the radiation can be used to decompose the surface of the element. In some embodiments, at least a portion of the surface of the polymeric matrix is decomposed, removing between about 1% to about 40% (e.g., vertical thickness) of the surface, thereby exposing more of the photocatalytic composition embedded therein. In some embodiments, about 1% of the surface is decomposed, about 2% of the surface is decomposed, about 3% of the surface is decomposed, about 4% of the surface is decomposed, about 5% of the surface is decomposed, about 10% of the surface is decomposed, about 15% of the surface is decomposed, about 20% of the surface is decomposed, about 25% of the surface is decomposed, about 30% of the surface is decomposed, about 35% of the surface is decomposed, about 40% of the surface is decomposed. In some embodiments, the amount of polymeric matrix removed from the photocatalytic element can be any combination of the aforementioned amounts, up to about 40%.

In some embodiments, the photodegradable surface can be modified and/or degraded by electromagnetic radiation. In some embodiments, the radiation can be used to decompose the polymeric surface of the element. In some embodiments, the surface of the polymeric matrix can be decomposed, removing between about 0.01 nm to about 1 mm of the surface, thereby exposing more of the photocatalytic composition embedded therein. In some embodiments, about 0.01 nm of the surface can be decomposed, about 0.02 nm of the surface can be decomposed, about 0.03 nm of the surface can be decomposed, about 0.04 nm of the surface can be decomposed, about 0.05 nm of the surface can be decomposed, about 0.1 nm of the surface can be decomposed, about 0.2 nm of the surface can be decomposed, about 0.3 nm of the surface can be decomposed, about 0.4 nm of the surface can be decomposed, about 0.5 nm of the surface can be decomposed, about 1 nm of the surface can be decomposed, about 2 nm of the surface can be decomposed, about 3 nm of the surface can be decomposed, about 4 nm of the surface can be decomposed, about 5 nm of the surface can be decomposed, about 10 nm of the surface can be decomposed, about 20 nm of the surface can be decomposed, about 30 nm of the surface can be decomposed, about 40 nm of the surface can be decomposed, about 50 nm of the surface can be decomposed, about 100 nm of the surface can be decomposed, about 200 nm of the surface can be decomposed, about 300 nm of the surface can be decomposed, about 400 nm of the surface can be decomposed, about 500 nm of the surface can be decomposed, about 1 micron of the surface can be decomposed, about 2 microns of the surface can be decomposed, about 3 microns of the surface can be decomposed, about 4 microns of the surface can be decomposed, about 5 microns of the surface can be decomposed, about 10 microns of the surface can be decomposed, about 20 microns of the surface can be decomposed, about 30 microns of the surface can be decomposed, about 40 microns of the surface can be decomposed, about 50 microns of the surface can be decomposed, about 100 microns of the surface can be decomposed, about 200 microns of the surface can be decomposed, about 300 microns of the surface can be decomposed, about 400 microns of the surface can be decomposed, about 500 microns of the surface can be decomposed, about 1 mm of the surface can be decomposed. In some embodiments, the surface of the photocatalytic element can be decomposed in any combination of the aforementioned ranges, up to about 1 mm.

In some embodiments, the method comprises irradiating the surface of the polymer matrix a sufficient amount of radiant energy to expose at least some photocatalytic nanoparticles. In some embodiments the thickness of polymeric matrix decomposed is less than about 100 nm. In some embodiments the sufficient amount of radiant energy is at least about 2.5 J/cm$^2$.

In some embodiments, an amount of radiant energy is provided to photoetch or decompose a sufficient amount of the matrix, uncovering the photocatalytic composition and contacting the composition with the desired material to be photocatalytically effected. The factors to consider in determining the amount radiant energy to be applied to the surface include the selected catalytic material, the matrix material. For example, for a 20 wt % photocatalytic material in a urethane acrylic resin (Unidic 17-806) at least about 25 W/m$^2$, 30 W/m$^2$, 40 W/m$^2$, 50 W/m$^2$ for at least about 1 hour, 2 hr and/or about 3 hours (light meter readings at the surface of the strips) is sufficient to enhance the photocatalytic activity of the photocatalytic element. For example, for a 20 wt % photocatalytic material in a urethane acrylic resin (Unidic 17-806) at least about 2.5 J/cm$^2$ to about 90 J/cm$^2$ can be sufficient to enhance the photocatalytic activity of the photocatalytic element. In some embodiments, the sufficient amount of radiant energy comprises at least about 59 W/m$^2$ for at least about 0.25 to about 2 hours.

In some embodiment, the substrates comprise polymer films which can be subject to pre-treatment for increasing the adhesion between coating and substrates. In some embodiments the pretreated films and or substrates can be chemically treated, corona treated or heated treated to increase adhesion of the coating to the substrates. Commercially available products of suitable chemically treated films include, but are not limited to, 3SAB/3SAC; 3LD4; 4407/4507; 2SABN/2SACN (Mitsubishi Polyester Films, Greer, S.C., USA). In some embodiment, the substrates can be pre-treated with coupling agents to promote the adhesion between polymer binders and substrates. In some embodiments, the couplings agents can be aminopropyltriethoxy silane, allyltrimethoxysilane, (3-aminopropyl)triethoxysilane, 3-aminopropyl(diethoxy)methylsilane, and/or (3-amino)trimethoxysilane.

In some embodiments, the radiant energy can be provided to photoetch or decompose a sufficient amount of the matrix under at least about 10% relative humidity, at least about 20% relative humidity, at least about 30% relative humidity, at least about 40% relative humidity, at least about 50% relative humidity. In some embodiments, the radiant energy can be provided to photoetch or decompose a sufficient amount of the matrix under at least about at least about 20% to about 80% relative humidity, 30% to about 70% relative humidity, at least about 40% to about 60% relative humidity, e.g., about 54.5% relative humidity and/or any combination of the above upper and for lower limits.

In some embodiments, applying the mixture to a substrate can further comprise casting the mixture upon the substrate. A suitable casting procedure can be described in U.S. Pat. No. 8,283,843, issued Oct. 9, 2012, which is incorporated by reference in their entireties. In some embodiments, the blade gap can be between 0.5 mil to about 50 mils, between about 2.0 mils to about 35 mils; between about 3.5 mil to about 20 mils. In some embodiments, the photocatalytic coating can be formed by applying the photocatalytic suspension on substrates by wire wound lab rod with wire size in the range of 0.003 to 0.020 inches (Paul N. Gardner Inc.).

EXAMPLES

The embodiments are described below in greater detail using Examples and Comparative Examples. Note, however, that those embodiments are in no way limited by the following. Various numerical values used in the following examples may be replaced with the values (upper and lower limits) given in the foregoing embodiments.

Firstly, examples according to an embodiment, wherein the photocatalyst sheet comprises a base material; and a photocatalyst layer that contains at least a photocatalyst and is formed on at least one surface of the base material through an aerosol deposition method, are described below.

Example 1

Firstly, a PET nonwoven fabric (Toyobo Co., Ltd.; thickness 150 μm; basis weight 20 g/m$^2$) was prepared as the base material which is a porous film.

The PET nonwoven fabric was installed on the seat of the substrate holder inside the deposition chamber (22° C.) of the aerosol deposition apparatus (carrier gas: oxygen gas) prepared beforehand.

Here, the distance between the jet orifices of the deposition nozzle and the surface of the PET nonwoven fabric was adjusted to 20 mm.

Separately, 150 mL of a photocatalyst composition powder was prepared by mixing 100 parts by mass of a tungsten (VI) oxide (WO$_3$) powder (photocatalyst particles; median diameter 0.5 μm; BET specific surface area L64 m$^2$/g; Sigma Aldrich JAPAN) and 50 parts by mass of a cerium(IV) oxide (CeO$_2$) powder (co-catalyst particles; median diameter 0.2 μm, BET specific surface area 4.1 m$^2$/g; Sigma Aldrich JAPAN). The photocatalyst composition powder was charged into a 500-mL glass aerosol chamber.

Thereafter, with the gas pipe on-off valve closed, and the connecting tube on-off valve open, the mechanical booster pump and the rotary pump were driven to create a reduced pressure of 50 Pa inside the deposition chamber and the aerosol chamber.

After adjusting the oxygen gas flow rate to 7 L/min with a gas flowmeter, the gas pipe on-off valve was opened while vibrating the aerosol chamber with a shaker. This aerosolizes the photocatalyst composition powder inside the aerosol chamber, and the aerosol thus obtained was expelled through the deposition nozzle.

Incidentally, the pressure inside the aerosol chamber was about 50,000 Pa, and the pressure inside the deposition chamber was about 280 Pa. The temperature inside the deposition chamber was 25° C.

The aerosol through the deposition nozzle was blown onto the surface of the PET nonwoven fabric while moving the fixed PET nonwoven fabric on the seat at a speed (relative speed) of 4 mm/s in x-y directions by moving the stage of the substrate holder.

This procedure was repeated five times to laminate a photocatalyst layer of 1 μm thickness on the surface of the PET nonwoven fabric. Consequently, the photocatalyst sheet of Example 1 was prepared.

Example 2

A photocatalyst layer of 1 μm thickness was laminated on the surface of the PET nonwoven fabric in the same manner as in Example 1, except that only the tungsten(VI) oxide powder was used as the photocatalyst composition powder.

Thereafter, a cerium oxide dispersion of a cerium(IV) oxide powder in water (solid content 85 mass %) was applied onto the surface of the photocatalyst layer with an applicator. The surface was then dried under 60° C., 720 min conditions to laminate a co-catalyst layer (thickness 0.5 μm). Consequently, the photocatalyst sheet of Example 2 was prepared.

Example 3

A photocatalyst composition powder as a mixture of a tungsten(VI) oxide powder (50 parts by mass) and a cerium (IV) oxide powder (50 parts by mass) was dispersed in water to obtain a photocatalyst dispersion (solid content 85 mass %). The dispersion was then dried to obtain a uniformly mixed powder of cerium(IV) oxide and tungsten(VI) oxide.

The photocatalyst sheet of Example 3 was produced in the same manner as in Example 1, except that this uniformly mixed powder of cerium(IV) oxide and tungsten(VI) oxide was used as the photocatalyst composition powder.

Example 4

In Example 4, firstly, 25 g of $TiO_2$ powder (photocatalyst, average particle diameter: 0.03 m, Nippon Aerosil Co., Ltd.) and 250 ml of ion exchange water were put in a 500-ml eggplant flask, stirred at room temperature to uniformly disperse the particles, thereby preparing an aqueous dispersion of $TiO_2$ powder.

Then, 0.68 g of copper(II) chloride dihydrate (Wako Pure Chemical Industries, Ltd.) was dissolved in 5 ml of ion exchange water, and the aqueous solution of copper(II) chloride dehydrate was added to the aqueous dispersion of $TiO_2$ powder. Subsequently, it was stirred for 1 hour while heated at 90° C., thereby preparing liquid A.

Then, an aqueous solution of sodium hydrate prepared by dissolving 1.255 g of sodium hydrate in 25 ml of ion exchange water was added to the liquid A, and then the pH of the solution was increased from 3 to 11, thereby preparing liquid B.

Then an aqueous solution of glucose prepared by dissolving 6.275 g of glucose (Wako Pure Chemical Industries, Ltd.) in 37.5 ml of ion exchange water was added to the liquid B. It was further stirred for 1 hour while heated at 90° C., whereby particles of copper(I) oxide and copper(II) oxide were precipitated on the surfaces of the particles of titanium oxide.

Next, the particles after the reaction were filtrated, then subjected to sufficient water washing, and the particles were then dried at 100° C. Consequently, a $Cu_xO$-supporting $TiO_2$ powder (co-catalyst-supporting type photocatalyst) was produced. According to the result of ICP analysis, it was confirmed that 1.0 part by weight of particles of copper oxide were supported with respect to 100 parts by weight of particles of titanium oxide.

A photocatalyst layer of 1 μm thickness was laminated on the surface of the PET sheet in the same manner as in Example 1, except that the photocatalyst composition powder produced above was used and also a non-porous film PET sheet (Toray Industries, Inc.; thickness 100 μm) was used as the base material. Consequently, the photocatalyst sheet of Example 4 was prepared. Scanning electron microscopy of the photocatalyst layer in the photocatalyst sheet of Example 4 confirmed that the co-catalyst $Cu_xO$ particles were supported on the photocatalyst $TiO_2$ particles.

Example 5

In Example 5, a $Cu_xO$-supporting $SnO_2$ powder (photocatalyst composition powder) was produced in the same manner as in Example 4, except that a $SnO_2$ powder (photocatalyst, average particle size 0.015 μm; Kanto Kagaku) was used in place of the $TiO_2$ powder. ICP analysis of the product powder confirmed that 1.0 weight part of copper oxide particles were supported with respect to 100 weight parts of the tin oxide.

A photocatalyst layer of 1 μm thickness was laminated on the surface of the PET sheet in the same manner as in Example 1, except that the photocatalyst composition powder produced above was used and also a non-porous film PET sheet (Toray Industries, Inc.; thickness 100 μm) was used as the base material. Consequently, the photocatalyst sheet of Example 5 was prepared. Scanning electron microscopy of the photocatalyst layer in the photocatalyst sheet of Example 5 confirmed that the co-catalyst $Cu_xO$ particles were supported on the photocatalyst $SnO_2$ particles.

Example 6

A photocatalyst layer of 1 μm thickness was laminated on the surface of the PET sheet in the same manner as in Example 1, except that a photocatalyst composition powder prepared by mixing 100 parts by mass of tungsten(VI) oxide ($WO_3$) (photocatalyst particles; median diameter 0.25 μm; Kojundo Chemical Laboratory Co., Ltd.), and 100 parts by mass of cerium(IV) oxide ($CeO_2$) (co-catalyst particles; median diameter 0.025 μm; Sigma Aldrich JAPAN) was used as the photocatalyst composition powder, and also a non-porous film PET sheet (Toray Industries, Inc.; thickness 100 μm) was used as the base material. Consequently, the photocatalyst sheet of Example 6 was prepared.

Comparative Example 1

A photocatalyst composition powder prepared by mixing 50 parts by mass of a tungsten(VI) oxide powder and 50 parts by mass of a cerium(IV) oxide powder was dispersed in water to obtain a photocatalyst dispersion (solid content 85 mass %).

The photocatalyst dispersion was applied to the PET nonwoven fabric with an applicator, and dried under 60° C., 720 min conditions to laminate a photocatalyst layer of 1 μm thickness on the surface of the PET nonwoven fabric. Consequently, the photocatalyst sheet of Comparative Example 1 was prepared.

Comparative Example 2

A tungsten(VI) oxide powder was dispersed alone in water to obtain a photocatalyst dispersion (solid content 85 mass %).

The photocatalyst dispersion was applied to the PET nonwoven fabric with an applicator, and dried under 60° C., 720 min conditions to laminate a photocatalyst layer of 1 μm thickness on the surface of the PET nonwoven fabric.

Thereafter, a co-catalyst layer (thickness 0.5 μm) was laminated on the surface of the photocatalyst layer in the same manner as in Example 2. Consequently, the photocatalyst sheet of Comparative Example 2 was prepared.

Comparative Example 3

A photocatalyst layer of 1 μm thickness was laminated on the surface of the PET nonwoven fabric in the same manner as in Comparative Example 1, except that the mixed powder of tungsten(VI) oxide and cerium(IV) oxide obtained in Example 3 was used as the photocatalyst composition powder. Consequently, the photocatalyst sheet of Comparative Example 3 was prepared.

Comparative Example 4

A photocatalyst layer of 1 µm thickness was laminated on the surface of the PET sheet in the same manner as in Comparative Example 1, except that the photocatalyst composition powder obtained in Example 4 was used and also the PET sheet used in Example 4 was used. Consequently, the photocatalyst sheet of Comparative Example 4 was prepared.

Evaluation

Adhesion of Photocatalyst Layer

The photocatalyst sheets of Examples and Comparative Examples were each placed in water, and cleaned with an ultrasonic cleaner operated in 33 cycles, each cycle consisting of 28 Hz for 3 seconds, 45 Hz for 3 seconds, and 100 Hz for 3 seconds (9 seconds in each cycle, a total of about 5 minutes).

The photocatalyst sheets of Examples and Comparative Examples were then each stretched in thickness direction on the photocatalyst layer surface side (co-catalyst layer surface side in Example 2 and Comparative Example 2) with a Digital Pull-Off Adhesion Tester (PosiTest AT-A; Defelsko).

Each photocatalyst sheet was then visually inspected for any detachment of the photocatalyst layer from the base material. There was no detachment in the photocatalyst sheets of Examples 1 to 6, and these sheets had excellent adhesion. On the other hand, detachment was observed in the photocatalyst sheets of Comparative Examples 1 to 4, and the adhesion was poor.

XRD Measurement

The photocatalyst sheets of Examples were evaluated through the crystal XRD measurement of the photocatalyst layer. The measurement confirmed crystallinity in the photocatalyst layer, showing that the photocatalyst layer sufficiently exhibited photocatalytic activity.

Photocatalytic Activity Measurement

The photocatalyst sheets of Examples and Comparative Examples were each measured for VOC decomposition ability to evaluate photocatalytic activity, as follows.

The photocatalyst sheet of interest for photocatalytic activity measurement was placed in a 5-L Tedlar bag. The bag was sealed, and the air inside the bag was released to create a vacuum. The same Tedlar bag was then charged with 3 L of compressed air and calibration acetaldehyde, and the acetaldehyde concentration was adjusted to 100 ppm. The acetaldehyde concentration was measured with a calibration gas chromatograph equipped with a flame ionization detector (GC-FID; GC-2010 plus available from Shimadzu Corporation).

After being allowed to stand in the dark for 1 hour to stabilize the acetaldehyde concentration (equilibrium state), the Tedlar bag was irradiated with light of a diode array that emits monochromatic blue light (wavelength 455 nm, irradiation intensity 10 mW/cm$^2$). After 1-hour irradiation, the gas inside the Tedlar bag was collected, and the residual acetaldehyde concentration was analyzed by GC-FID.

The acetaldehyde decomposition rate (%) was calculated according to the following equation A.

Acetaldehyde decomposition rate (%)=$(X-Y)/X \times 100$.    Equation A

In the equation, X is the acetaldehyde concentration before the irradiation (100 ppm), and Y is the acetaldehyde concentration after the irradiation.

It can be said that, the higher the acetaldehyde decomposition rate is, the higher the VOC decomposition ability is, i.e., the higher the photocatalytic activity is, and conversely, the lower the acetaldehyde decomposition rate is, the lower the VOC decomposition ability is, i.e., the lower the photocatalytic activity is.

The decomposition rate was 90% in Example 1, 100% in Example 2, 100% in Example 3, 60% in Example 4, 60% in Example 5, and 70% in Example 6. In Comparative Examples, the decomposition rate was 5% in Comparative Example 1, 80% in Comparative Example 2, 80% in Comparative Example 3, and 60% in Comparative Example 4.

The photocatalyst layer adhesion and the acetaldehyde decomposition rate of the photocatalyst sheets of Examples and Comparative Examples are summarized in Table 1 below.

TABLE 1

|  | Photocatalyst layer adhesion | Acetaldehyde decomposition rate (%) |
| --- | --- | --- |
| Ex. 1 | Good | 90 |
| Ex. 2 | Good | 100 |
| Ex. 3 | Good | 100 |
| Ex. 4 | Good | 60 |
| Ex. 5 | Good | 60 |
| Ex. 6 | Good | 70 |
| Com. Ex. 1 | Poor | 5 |
| Com. Ex. 2 | Poor | 80 |
| Com. Ex. 3 | Poor | 80 |
| Com. Ex. 4 | Poor | 60 |

As can be seen in the results presented in Table 1, in the photocatalyst sheets of Examples 1 to 6 in which the photocatalyst layer was formed by using the aerosol deposition method, the photocatalytic activity tended to be more excellent as compared to the photocatalyst sheets of Comparative Examples, and the photocatalyst layer had more excellent adhesion to the surface of the base material. On the other hand, in the photocatalyst sheets of Comparative Examples 1 to 4 in which the photocatalyst layer was formed by applying the photocatalyst dispersions, the adhesion of the photocatalyst layer to the base material surface was inferior, and the photocatalytic activity tended to be lower as compared with the photocatalyst sheets of the Examples.

Next, Examples relating to Method A are described Belo

Example A 100 mg of PES powder was mixed in 10 ml of cyclopentanone in a scintillation vial, subjected to ultrasonics for about 20 minutes. The sample was removed from the ultrasonic source and examined for residual powder.

Example B-G

Examples B-G were screened in a similar manner to that described in Example A above, except that the same amount (about 100 mg) of the various thermoplastic materials (ethylene vinyl acetate [EVA]; polycarbonate [PC]) instead of PES were subjected to various solvents (dichloromethane [DCM]; methyl ethyl ketone [MEK]) instead of cyclopentanone. The results are shown in Table 2 below.

TABLE 2

| Example | solvent | Thermoplastic material | dissolution |
|---|---|---|---|
| B | Dichloromethane | PES | substantially |
| C | Cyclopentanone | EVA | substantially |
| D | Toluene | EVA | substantially |
| E | Methyl ethyl ketone | EVA | substantially |
| F | Methyl ethyl ketone | PC | substantially |
| G | Methyl ethyl ketone | PC | substantially |

***Copper Loaded P25: The impregnation of the copper oxide nanoparticles was accomplished by the following procedure: The weight fraction of copper to plural phasic n-type semiconductor (87% anatase phase $TiO_2$/13% rutile phase $TiO_2$ [BET SSA about 45 $m^2/g$] sold under the brand name "P25" [EvoniK Degussa, N.J., USA]) was 0.01. 10 mL aqueous solution of $CuCl_2$-$2H_2O$ (26.8 mg) was stirred with 1 g of processed P25 $TiO_2$ at 90° C. for about 1 h. Then, 1.5 ml of aqueous solution containing NaOH (50 mg) and glucose (250 mg) was added to the reaction mixture at 90° C. while stirring. After the addition of aqueous solution of glucose and NaOH, the mixture was stirred for another about 1 h, then cooled down to room temperature, followed by filtration through 0.2 micron membrane, washing with 100 to 150 mL DI water and finally dried it at 110° C. in air oven overnight (10 to 15 h).

Example A-1

A slurry of copper loaded P25 was prepared by mixing 500 mg of copper loaded P25 in 10 g of cyclopentanone in a scintillation vial, which was then subjected to ultrasonics for 1 hour. The milky suspension was then spin coated onto a sheet of polyethersulfone (PES). The spin coating was as follows: step 1) an about 10 second ramp to 400 rpm, dwell for about 20 seconds; step 2) an about 10 second ramp to 1200 rpm, dwell for about 40 seconds. After spin coating, the coated sheet was immediately placed on a hot plate for about 10 minutes at 120° C., and then it was placed in an air-circulating oven for about 1 hour at 110° C. Exposure of the thermoplastic material to the solvent was about 2 minutes before heating.

Example A2-A8

All examples were prepared and heat treated according to the exact same procedure outlined in Example 1. All examples in this series resulted in killing 99.9% of E. coli after 2 hours at 800 lx illumination.

A-2) 2 wt % copper loaded P25 in dichloromethane coated on PES

A-3) 5 wt % copper loaded P25 in dichloromethane coated on PES

A-4) 2 wt % copper loaded P25 in cyclopentanone coated on PES

A-5) 5 wt % copper loaded P25 in toluene coated on ethylene vinyl acetate (EVA)

A-6) 2 wt % copper loaded P25 in cyclopentanone coated on EVA

A-7) 2 wt % copper loaded P25 in toluene coated on EVA

A-8) 5 wt % copper loaded P25 in cyclopentanone coated on polycarbonate (PC)

Example A9-A11

Showed between 1% and 99.8% killing performance after 2 hours under 800lx illumination.

A-9) 2 wt % copper loaded P25 in methyl ethyl ketone coated on PC

A-10) 2 wt % copper loaded P25 in methyl ethyl ketone coated on EVA

A-11) 5 wt % copper loaded P25 in methyl ethyl ketone coated on EVA

Next, the embodiments relating to Method B will be explained with respect to certain examples which are not intended to limit the present invention. Further, in the present disclosure where conditions and/or structures are not specified, the skilled artisan in the art can readily provide such conditions and/or structures, in light of the teachings herein, as a matter of routine experimentation.

Synthesis of Photocatalytic Particles
Copper Loaded P25

A mixture of 83% Anatase and 17% Rutile $TiO_2$ (this mixture is often referred to as Aeroxide $TiO_2$) was purchased from Evonik as product number Aeroxide® TiO2 P 25. It is a nanopowder with average BET SSA of 45 $m^2/g$. The $TiO_2$ particles were further loaded with 1 wt % copper oxide nanoparticles using the following procedure: The weight fraction of Copper to processed P25 $TiO_2$ (1 g) was 0.01. 10 mL aqueous solution of $CuCl_2.2H_2O$ (26.8 mg) was stirred with 1 g of processed P25 $TiO_2$ at 90° C. for 1 hour. Then, 1.5 ml of aqueous solution containing NaOH (50 mg) and glucose (250 mg) was added to the reaction mixture at 90° C. while stirring. After the addition of aqueous solution of glucose and NaOH, the mixture was stirred for another 1 hour, then cooled down to room temperature, followed by filtration through a 0.2 micron membrane, and washing with 100 to 150 mL DI water and finally dried at 110° C. in air oven overnight (10 to 15 hours).

Donor Sheet

A Kapton polyimide sheet was purchased from CS Hyde Company as Kapton (polyimide) film type HN item #18-3F-24 and used as the donor sheet.

Thermoplastic Element

A 254 •m thick PES ULTRASON (polyethersulfone resin) sheet was purchased from CS Hyde Company product film item #35-10F-24 and used as the thermoplastic element.

A 254 •m thick photovoltaic grade (high molecular weight) polycarbonate (PC) sheet was purchased from CS Hyde Company as product film item #38-10F-GG and used as the thermoplastic substrate.

Example B1

A particle embedded thermoplastic element was prepared according to the following procedure. A slurry of copper loaded P25 was prepared by mixing 100 mg of copper loaded P25 in 10 g of methanol in a scintillation vial, which was then subjected to ultrasonication for 1 hour. The milky suspension was then spin coated onto a sheet of Kapton polyimide. The spin coater recipe was as follows: step 1) 10 second ramp to 400 rpm, dwell for 20 seconds; step 2) 10 second ramp to 1200 rpm, dwell for 40 seconds. The coated Kapton polyimide sheet was placed on a hot plate for 10 minutes at 120° C. until all traces of solvent were removed. Then, the resulting Kapton polyimide sheet with the loosely attached particles was placed with the coated side down on the surface of the polyethersulfone (PES) sheet. Similarly to the setup shown in FIG. 11, another uncoated Kapton polyimide sheet was placed on the opposite side of the PES sheet and this along with a 250 micron spacer was placed on the lower platen of a Carver heated pressing means that was heated to 280° C. (which is the softening temperature of PES). Once the Carver heated pressing means reached the 280° C. temperature, the Kapton-sandwiched PES and spacer were then simultaneously subjected to a pressure and temperature of 3,000 psi at 280° C. After a sufficient amount of time had passed to ensure the photocatalytic particles were embedded into the PES sheet, the pressure was released and the heat was removed. Once the temperature of the PES decreased, the sheets were removed from the press and peeled apart, resulting in a PES sheet having photocatalytic particles permanently embedded in its surface.

Example B2

A particle embedded thermoplastic element was prepared similarly to the procedure used in Example B1, except a polycarbonate (PC) sheet was used as the thermoplastic element.

Example B3

A particle embedded thermoplastic element was prepared similarly to the procedure used in Example B2, except 2 wt % copper loaded P25 particles were used instead of 1 wt % copper loaded P25.

Example B4

A particle embedded thermoplastic element was prepared similarly to the procedure used in Example B1, except 2 wt % copper loaded P25 particles were used instead of 1 wt % copper loaded P25.

Example B5

A particle embedded thermoplastic element was prepared according to the following procedure. A slurry of copper loaded P25 was prepared by mixing 100 mg of copper loaded P25 in log of 1:4 methanol:n-butanol in a scintillation vial, which was then subjected to ultrasonication for 1 hour. The milky suspension was then blade coated onto a sheet of Kapton polyimide, with a blade height of about 1-3 mm. The coated Kapton polyimide sheet was placed on a hot plate for 10 minutes at 120° C. until all traces of solvent were removed. Then, the resulting Kapton polyimide sheet with the loosely attached particles was placed with the coated side down on the surface of the polyethersulfone (PES) sheet. Similarly to the setup shown in FIG. 10, another uncoated Kapton polyimide sheet was placed on the opposite side of the PES sheet and this was placed on the lower platen of a Carver heated pressing means that was heated to 280° C. (which is the softening temperature of PES). Once the Carver heated pressing means reached the 280° C. temperature, the Kapton-sandwiched PES were then simultaneously subjected to a pressure and temperature of 3,000 psi at 280° C. After a sufficient amount of time had passed to ensure the photocatalytic particles were embedded into the PES sheet, the pressure was released and the heat was removed. Once the temperature of the PES decreased, the sheets were removed from the press and peeled apart, resulting in a PES sheet having photocatalytic particles permanently embedded in its surface.

Next, Examples relating to Method C are described below.

Embodiments of optical elements described herein improve the ability of colorblind individuals to distinguish a first color from a second color having a different wavelength. These benefits are further shown by the following examples, which are intended to be illustrative of the embodiments of the disclosure, but are not intended to limit the scope or underlying principles in any way.

Example C1

Example (A) (P-CAT ($Cu_xO/TiO_2$) Coating on PET Substrate)

Commercial available polyethylene terephthalate (PET) film (Eplastics Inc. San Diego, Calif. USA) with a thickness of about 120 micrometers (microns) was used as substrate for a photocatalytic coating. The substrate was cut into paper size, e.g., about 5 cm×7.5 cm. The cut PET substrate was cleaned with acetone and then dried.

A binder solution containing 10 wt % polymer matrix was made by mixing about 1.0 gm of a uv-curable urethane acrylate binder (sold under the brand designation, Unidic17806, by DIC International (USA), LLC, Parsippany, N.J., USA) with about 5 gm cyclopentanone (reagent>99.5%, Sigma-Aldrich, St. Louis, Mo., USA) and about 24 mg Ir 907 photoinitiator. The mixing was conducted with planetary centrifugal mixer (THINKY AR-310) at about 2000 rpm for 2 min for mixing and then at about 2200 rpm for about 1 min for defoaming.

To make a coating suspension, one part of $CuxO/P25$ photocatalytic powder (about 0.2 gm) by weight, 10 mg of dispersing agent (Flowen G700) was mixed with 5 part by weight (about about 5 g), of binder solution described above (10 wt % urethane acrylate dissolved in cyclopentanone). The photocatalytic powder was made according to that described in U.S. patent application Ser. No. 13/840,859, filed Mar. 15, 2013; and U.S. Provisional Application 61/835,399, filed Jun. 14, 2013; and U.S. patent application Ser. No. 13/741,191, filed Jan. 14, 2013 (United States Publication No. 2013/0192976, published Aug. 1, 2013). The photocatalytic-cat powder comprises copper oxide loaded titanium oxide doped with carbon, nitrogen and tin to increase the light absorption in visible light range. The nominal copper content in P-cat was 1 wt %. 0.2 gm of photocatalytic powder was dispersed in the binder solution (about 1 gm, 10% solution) by keeping the glass vial containing the mixture in a sonication bath for about half hour followed by probe sonication for about 20 mins. The obtained suspension was passed through a filter with opening of 5 micrometers.

Prior coating, the cleaned PET substrate was subject to corona discharge treatment to increase the hydrophilicity of substrate surface for good wettability of coating suspension. A corona treatment apparatus (TEWC-4AX, KASUGA DENKI Inc. JAPAN) was used at discharge power of 100 W and scan speed of 0.5 m/sec for two scans.

The coating of the substrate (Ex-C1) was performed on the prepared PET substrate by tape casting with use of doctor blade and tape caster (AFA-II, MTI Corporation) by the method described in U.S. Pat. No. 8,283,843, filed Jan. 28, 2011, issued Oct. 9, 2012. The gap of doctor blade was kept in the range of 3 mil to 20 mils (one mil equals to 1/1000 inch or 25.4 micrometers). The PET substrate with photocatalytic coating was dried at ambient atmosphere for about 10 minutes until dry; heated at about 90 to 100° C. for about 2 min, then uv cured under Loctite® Zeta® 7411 UV Flood Curing System. The UV light energy was monitored by the ZETA 7011-A Dosimeter-Radiometer with the energy intensity about 20 mw/$cm^2$.

Comparative Example C1 (CE-C1) PCat Coated Slides 20 mg of the photocatalytic material described above (CuxO/P25) was mixed in 10 mL of 100% ethanol (Sigma Aldrich, St. Louis Mo., USA) and sonicated for about 20 minutes. 5×100 microliter samples (about 1 mg photocatalytic material total) of the photocatalytic material/ethanol suspension were deposited upon a slide and dried at room temperature.

Films 14 films (about 5×7.5 cm) were prepared films in a manner similar to Ex-C1 above, Two film samples were not exposed to the xenon light (Ex-C1A1, Ex-C1A2). Two each of the remaining film samples were placed in a xenon flatbed (model: Atlas SUNTEST XXL+, Atlas Material Testing Technology LLC, Chicago, Ill., USA) for photodegrading the coated PET examples, with the following settings:

Irradiance [w/m$^2$]: 59.9
Chamber temperature[° C.]: 38.6
Black panel temp[° C.]: 61.5
Relative humidity[%]: 54.5

Two pieces were each removed at 0.25 h (Ex-C1B1 and Ex-C1B2), 1 h (Ex-C1C1 and Ex-C1C2), 2 h (Ex-C1D1 and Ex-C1D2), 4 h (Ex-C1E1 and Ex-C1E2), 8 h (Ex-C1F1 and Ex-C1F2), 24 h (Ex-C1G1 and Ex-C1G2) after initial insertion within the chamber and SEM, haze, t %, hardness, adhesion data for one sample from each time interval was recorded. T % and Haze displayed a noticeable change after 8 hrs. Hardness of the samples, appeared to remain the same until about 8 hrs. Adhesion became worse after only about one hour. SEM morphology (SEM 3A, 3B, and 3C are SEM's of Examples C1A, C1E and C1F, respectively) showed an absence of clear cavity until about 4 hrs, with an appearance of numerous cavities about 8 hrs. The SEM images also showed that the photodegradation appeared gradually. We expected the very top layer of binder to be etched away substantially uniformly so that the pcat particle was exposed to provide an increased antimicrobial performance. Surprisingly, the degradation started initially adjacent the Pcat particle vicinity and formed an annular cavity adjacent the particle. The antimicrobial data showed the killing performance was improved after photoetching up to about 2 hours of photoetching exposure. Preliminary data showed Chemical (IPA/Bleach) acceptable durability test up to about two hours of etching. The results are shown in Table 3 below.

Antibacterial performance was evaluated by following the procedures

One CE-C1 sample made as described above (no exposure to xenon flatbed) and one sample each (7 total) of the coated substrates (Examples C1A, C1B, C1C, C1D, C1E, C1F and C1G) were removed from the chamber at the respective time intervals as described above, were placed in a glass dish with a water soaked filter paper for maintaining moisture, and glass spacers were inserted between the substrate and the filter paper to separate them.

E. coli (ATCC 8739) was streaked onto a 10 cm diameter petri dish containing about 20 ml of LB (lysogeny broth/luria broth) agar, and incubated at about 37° C. overnight. For each experiment, a single colony was picked to inoculate about 3 mL nutrient broth, and the inoculated culture was incubated at about 37° C. for about 16 hours to create an overnight culture (~10$^9$ cells/mL). A fresh log-phase culture of the overnight culture was obtained by diluting the overnight culture ×100, inoculating another 5 cm petri dish with LB agar and incubated about at 37° C. for about 2.5 hr. The fresh culture was diluted 50× with 0.85% saline, which will gave a cell suspension of about 2×10$^6$ cells/mL. 50 μL of the cell suspension was pipetted onto each deposited glass substrate. A sterilized (in 70% and then 100% EtOH) plastic film (20 mm×40 mm) was placed over the suspension to spread evenly under the film. The specimen was kept in the dark (CuxO$_2$-Dark) or then irradiated under blue LED light (455 nm, 10 mW/cm$^2$) (CuO$_2$-light). At chosen time point, e.g., 30 min/60 min increments, the specimen was placed in 10 mL of 0.85% saline and vortexed to wash off the bacteria. The wash off suspension was retained, then serially diluted using 0.85% saline, and then plated on LB agar and incubated at about 37° C. overnight to determine the number of viable cells in terms of CFU/Specimen.

Figure 15:
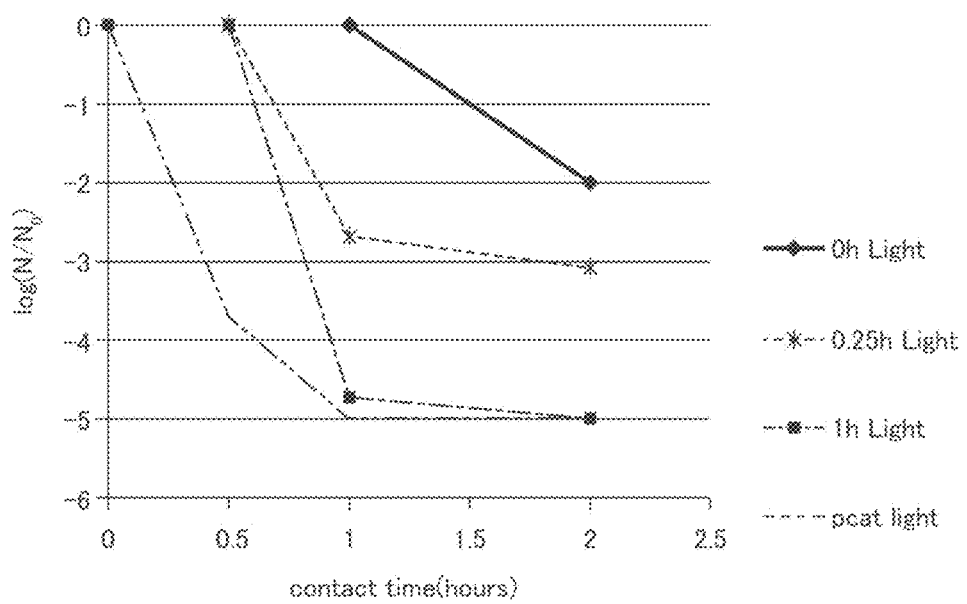
FIG. 15 is a graph of antimicrobial activity of an embodiment of a photocatalytic element described herein.

FIG. 15 shows the antibacterial (*E. Coli*) performance of embodiments described above with varied exposure times to radiant energy within the xenon flatbed instrument (Examples C1A [0 hr], C1B [0.25 hr], C1C [1 hr], CE-C1 (Photocatalytic materials without polymer/exposure).

Figure 16:
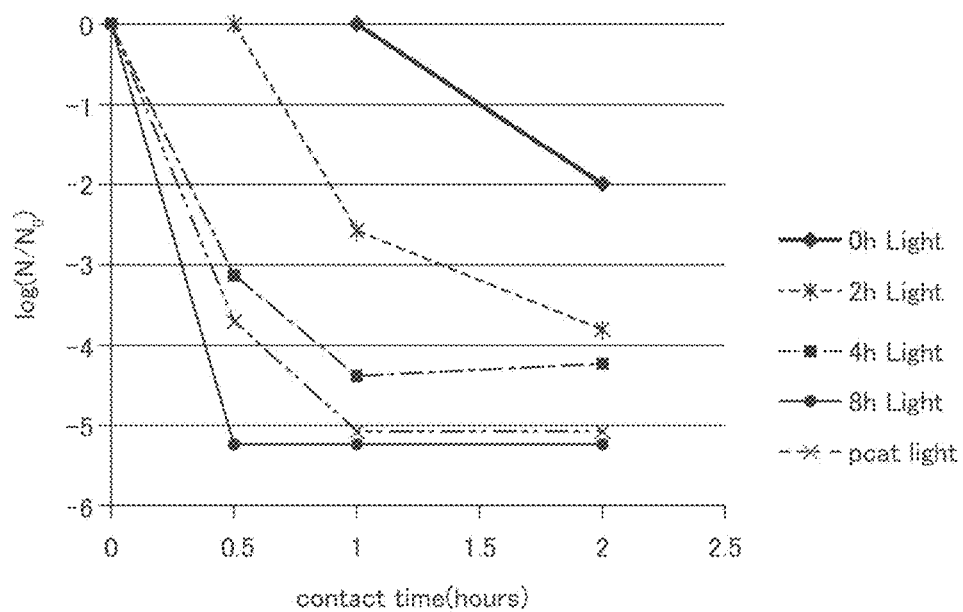
FIG. 16 is a graph of antimicrobial activity of an embodiment of a photocatalytic element described herein.

FIG. 16 shows the antibacterial (*E. Coli*) activity of embodiments described herein (Examples C1A [0 hr], C1D [2 hr], C1E [4 hr], C1F [8 hr]) and CE-C1 under light.

Chemical Durability Test

Films made in accordance with Examples C8A, C8D, C8E and C8F above were each swabbed with a cotton swab dipped in bleach or IPA, respectively, then wiped with a clean/undipped cotton swab 20 times. Each film was then was soaked in the respective chemical for certain specified time. After soaking, each film was wiped with a clean/undipped cotton swab 20 times again.

Each sample was examined visually. If there was no apparent scratch, damage, nor any appearance change, the test was considered a pass. The results of the durability tests are shown in Table 4 below.

TABLE 3

| Sample name | Exposed Time in yellow chamber | T % 550 nm | haze | hardness | adhesion | SEM | Killing data (light only) |
|---|---|---|---|---|---|---|---|
| Example C1A | 0 h | 84 | 22 | 3H | 3B | control | 2 h/2log |
| Example C1B | 0.25 h | 82 | 26 | 3H | 4B | No clear change | 2 h/3log |
| Example C1C | 1 h | 83 | 22 | 3H | 3-4B | No clear change | 2 h/5log |
| Example C1D | 2 h | 83 | 23 | 3H | 1B | No clear change | 2 h/3log |
| Example C1E | 4 h | 83 | 21 | 4H | 0B-1B | Cavity started | 0.5 h/3log |
| Example C1F | 8 h | 85 | 18 | 3H | 2B | Lots of cavity | 0.5 h/5log |
| Example C1G | 24 h | 73 | 73 | <2B | 0B | damaged | 0.5 h/4log |

TABLE 4

| | Soaking time in solvents | Bleach | IPA |
|---|---|---|---|
| Example C8A | 4 h | pass | pass |
| | 8 h | pass | pass |
| | 24 h | pass | pass |
| Example C8D | 4 h | pass | pass |
| | 8 h | pass | pass |
| | 24 h | pass | pass |

TABLE 4-continued

| | Soaking time in solvents | Bleach | IPA |
|---|---|---|---|
| Example C8E | 4 h | pass | pass |
| | 8 h | pass | pass |
| | 24 h | pass | pass |
| Example C8F | 4 h | Not test | pass |
| | 8 h | Not test | pass |
| | 24 h | Not test | pass |

Unless otherwise indicated, all numbers expressing quantities of ingredients, properties such as molecular weight, reaction conditions, and so forth used in the specification and claims are to be understood as being modified in all instances by the term "about" Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The present application is based on a U.S. provisional application No. 61/843,267 filed Jul. 5, 2013, a Japanese patent application No. 2013-218875 filed Oct. 22, 2013, a U.S. provisional application No. 61/898,980 filed Nov. 1, 2013, a U.S. provisional application No. 61/899,799 filed Nov. 4, 2013, a U.S. provisional application No. 61/899,804 filed Nov. 4, 2013, a U.S. provisional application No. 61/944,879 filed Feb. 26, 2014, a U.S. provisional application No. 61/946,611 filed Feb. 28, 2014, a U.S. provisional application No. 61/955,466 filed Mar. 19, 2014, and a Japanese patent application No. 2014-113003 filed May 30, 2014, the contents of which are incorporated herein by reference.

The invention claimed is:

1. A photocatalyst sheet comprising:
   a base material; and
   a photocatalyst layer that contains at least a photocatalyst,
   wherein the photocatalyst is formed on at least one surface of the base material by aerosol deposition performed at a pressure between 10 and 1,000 Pa,
   wherein the photocatalyst layer contains a co-catalyst,
   wherein the photocatalyst contains titanium(IV) oxide or tin(IV) oxide, and the co-catalyst contains copper(I) oxide or copper(II) oxide, and wherein the co-catalyst is supported on the photocatalyst, and
   wherein the mass ratio of photocatalyst to co-catalyst is about 1:1 to about 2:1.

2. The photocatalyst sheet according to claim 1, wherein the base material is a porous film.

3. The photocatalyst sheet according to claim 1, wherein the base material is formed of a resin.

4. The photocatalyst sheet according to claim 3, wherein the resin includes a thermosetting resin, a thermoplastic resin, an ultraviolet curable resin, or an electron beam curable resin.

5. The photocatalyst sheet according to claim 1, wherein the photocatalyst shows a visible-light responsiveness.

6. A method for producing the photocatalyst sheet of claim 1, the method comprising forming a photocatalyst layer containing at least a photocatalyst on at least one surface of a base material by aerosol deposition,
   wherein the aerosol comprises the photocatalyst, and
   wherein the aerosol deposition is performed at a pressure between 10 and 1,000 Pa.

7. A photocatalyst sheet comprising:
   a base material; and
   a photocatalyst layer that contains at least a photocatalyst,
   wherein the photocatalyst is formed on at least one surface of the base material by aerosol deposition performed at a pressure between 10 and 1,000 Pa,
   wherein the photocatalyst layer contains a co-catalyst,
   wherein the photocatalyst contains tungsten(VI) oxide, and the co-catalyst contains cerium(IV) oxide, and
   wherein the mass ratio of photocatalyst to co-catalyst is about 1:1 to about 2:1.

8. The photocatalyst sheet according to claim 7, wherein the base material is a porous film.

9. The photocatalyst sheet according to claim 7, wherein the base material is formed of a resin.

10. The photocatalyst sheet according to claim 9, wherein the resin includes a thermosetting resin, a thermoplastic resin, an ultraviolet curable resin, or an electron beam curable resin.

11. The photocatalyst sheet according to claim 7, wherein the photocatalyst shows a visible-light responsiveness.

12. A method for producing the photocatalyst sheet of claim 7, the method comprising forming a photocatalyst layer containing at least a photocatalyst on at least one surface of a base material by aerosol deposition,
wherein the aerosol comprises the photocatalyst, and
wherein the aerosol deposition is performed at a pressure between 10 and 1,000 Pa.

\* \* \* \* \*